(12) United States Patent
Schembri et al.

(10) Patent No.: US 6,518,056 B2
(45) Date of Patent: *Feb. 11, 2003

(54) APPARATUS, SYSTEMS AND METHOD FOR ASSAYING BIOLOGICAL MATERIALS USING AN ANNULAR FORMAT

(75) Inventors: Carol T. Schembri, San Mateo, CA (US); Arthur Schleifer, Portola Valley, CA (US)

(73) Assignee: Agilent Technologies Inc., Palo Alto, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/302,011

(22) Filed: Apr. 27, 1999

(65) Prior Publication Data

US 2002/0064774 A1 May 30, 2002

(51) Int. Cl.[7] ............................. C12M 1/34; C12Q 1/68; C12P 19/34; C07H 21/02; C07H 21/04
(52) U.S. Cl. .................... 435/287.2; 435/5; 435/7.1; 435/7.2; 435/6; 435/91.2; 536/22.1; 536/23.1; 536/24.3; 536/24.31; 536/24.32; 536/24.33
(58) Field of Search .................. 435/5, 6, 7.1, 7.2, 435/91.2, 287.2; 536/22.1, 23.1, 24.3, 24.31, 24.32, 24.33

(56) References Cited

U.S. PATENT DOCUMENTS

| | | |
|---|---|---|
| 4,940,322 A | 7/1990 | Miwa et al. |
| 5,143,854 A | 9/1992 | Pirrung et al. |
| 5,320,808 A | 6/1994 | Holen et al. |
| 5,340,747 A | 8/1994 | Eden |
| 5,384,261 A | 1/1995 | Winkler et al. |
| 5,405,783 A | 4/1995 | Pirrung et al. |
| 5,412,087 A | 5/1995 | McGall et al. |
| 5,429,807 A | 7/1995 | Matson et al. |
| 5,434,049 A | 7/1995 | Okano et al. |
| 5,451,683 A | 9/1995 | Barrett et al. |
| 5,508,200 A | 4/1996 | Tiffany et al. |
| 5,585,639 A | 12/1996 | Dorsel et al. |
| 5,653,939 A | 8/1997 | Hollis et al. |

(List continued on next page.)

FOREIGN PATENT DOCUMENTS

| | | |
|---|---|---|
| EP | 0 543 550 A1 | 5/1993 |
| WO | WO 95/11995 | 5/1995 |
| WO | WO95/33846 | * 12/1995 |

OTHER PUBLICATIONS

Stimpson, D.I. et al., "Parallel Production of Oligonucleotide Arrays Using Membranes and Reagent Jet Printing", BioTechniques, (1998), vol. 25, No. 5, pp. 886–890.

Primary Examiner—Jeffrey Siew

(57) ABSTRACT

An apparatus, systems and methods use an r, θ format for the manufacture and analysis of biological materials. The apparatus is an array of biological material in an annular region on a substrate. The apparatus is formed with a system for synthesizing arrays that includes a spinner assembly for rotating the substrate during the synthesis of the biological material thereon. The apparatus is hybridized with complementary biological material using a system for hybridizing that includes a spinner assembly to spin the apparatus after the complementary biological material is added. The hybridized apparatus is optically interrogated with a system for interrogation that includes a light source, optics, and a scanning assembly that holds and rotates the apparatus so that the light source can remain stationary. The method of assaying biological materials uses the systems for synthesizing, hybridizing and optically interrogating the apparatus in accordance with the invention.

21 Claims, 12 Drawing Sheets

U.S. PATENT DOCUMENTS

| | | |
|---|---|---|
| 5,658,802 A | 8/1997 | Hayes et al. |
| 5,670,322 A | 9/1997 | Eggers et al. |
| 5,677,197 A | 10/1997 | Gordon et al. |
| 5,744,305 A | 4/1998 | Fodor et al. |
| 5,760,951 A | 6/1998 | Dixon et al. |
| 5,763,870 A | 6/1998 | Sadler et al. |
| 5,812,272 A | 9/1998 | King et al. |
| 5,837,475 A | 11/1998 | Dorsel et al. |
| 6,068,818 A * | 5/2000 | Ackley et al. ............ 422/50 |
| 6,077,673 A * | 6/2000 | Chenchik et al. ............ 435/6 |

* cited by examiner

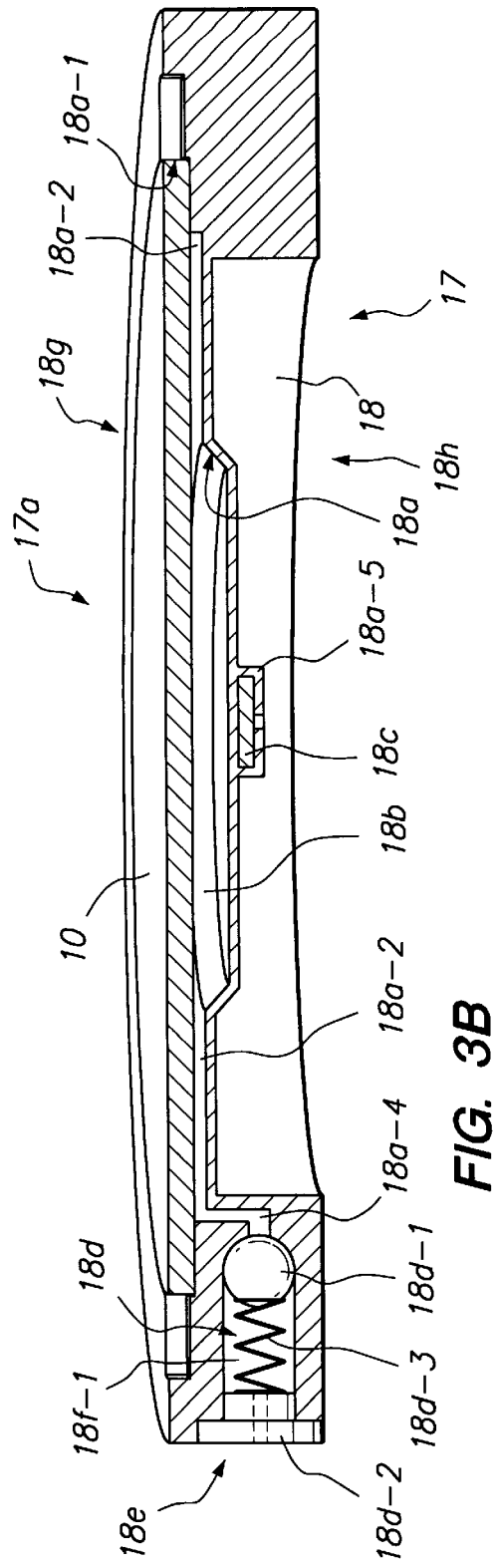
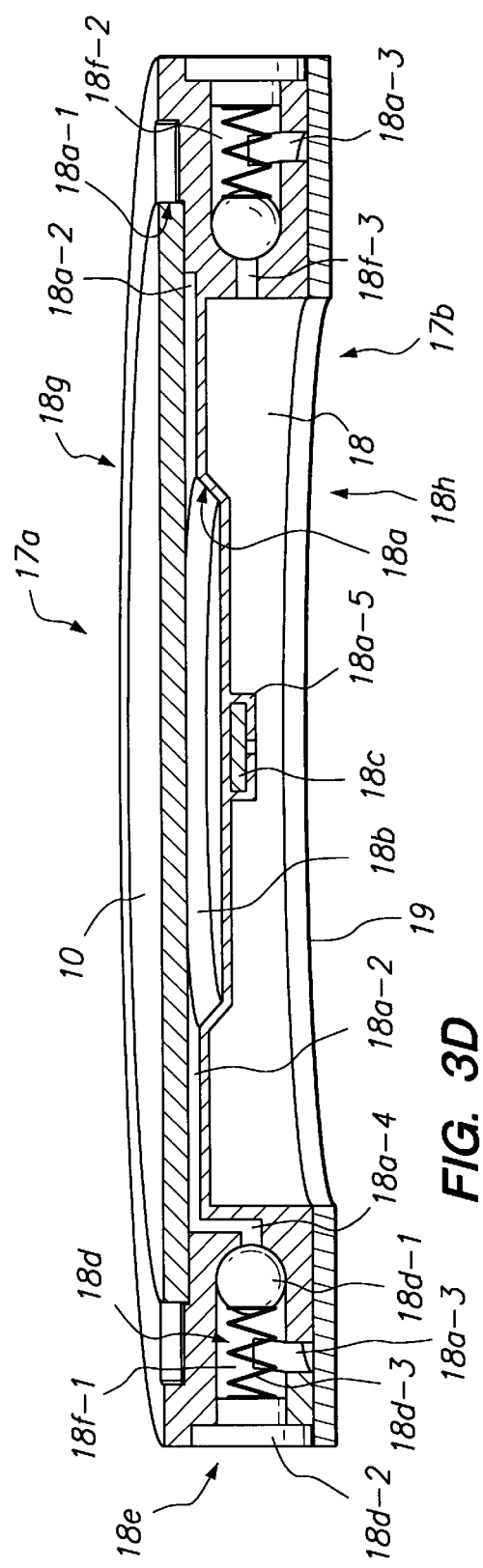
FIG. 3B
FIG. 3D

APPARATUS, SYSTEMS AND METHOD FOR ASSAYING BIOLOGICAL MATERIALS USING AN ANNULAR FORMAT

TECHNICAL FIELD

This invention relates to analytical tools and methods for assaying biological materials in a variety of applications. In particular, the invention relates to an apparatus, systems and a method for assaying biological materials for monitoring levels of gene expression and mutations in gene sequences using an annular format.

BACKGROUND ART

Conventional analysis of biological materials, such as DNA, RNA, proteins and the like, employs an apparatus having biological material on a substrate in an array pattern of discrete features. The features are typically chemically bound to the substrate. The features may be either "probes" of known molecular make-up or "targets" of unknown molecular make-up. For the purposes of simplicity, hereinafter the features bound to the substrate will be referred to as probes and the samples under test will be referred to as "targets". Arrays of biological probes are quickly becoming a powerful method of simultaneously assaying thousands of targets within a single biological sample. The surface bound probes are typically formed of DNA oligonucleotides, cDNA's, PCR products, antibodies, antigens, and the like.

The arrays are manufactured using automated equipment, such that the spatial location on the substrate of each type of surface bound probe is known within a certain margin of error. The sample containing the unknown quantities of the targets is modified so that each potential target molecule is labeled with a fluorescent label. The sample is applied to the array surface so that the targets may hybridize or bind to their complementary surface bound probe. After the reaction is complete, the surface of the array is washed. The hybridized array is interrogated optically to determine the level of hybridization and the locations and therefore, the identity of the hybridized targets. Optionally, the array substrate may be put into a package for handling, processing and optical interrogation. The array can be held in the package with an appropriate adhesive or glue.

Optical interrogation is typically performed with commercially available optical scanning systems, examples of which are described in U.S. Pat. Nos. 5,837,475, 5,760,951 (confocal scanner) and U.S. Pat. No. 5,585,639 (off axis scanner), all incorporated herein by reference. Typical scanning fluorometers are commercially available from different sources, such as Molecular Dynamics of Sunnyvale, Calif., General Scanning of Watertown, Mass., Hewlett Packard of Palo Alto, Calif. and Hitachi USA of So. San Francisco, Calif. Analysis of the data, (i.e., collection, reconstruction of image, comparison and interpretation of data) is performed with associated computer systems and commercially available software, such as IMAGEQUANT™ by Molecular Dynamics or GENECHIP™ by Affymetrix of Santa Clara, Calif. Typically, a laser beam is scanned across the array surface. The laser beam excites the fluorescent labels on the hybridized targets and the fluorescent signal is detected by a detector and processed by a computer. The intensity of the signal at each physical location in the array is a measure of the hybridization efficiency of a target with a known chemical probe. The intensity relates directly to the concentration of that target within the sample. The signal can be used to simply identify the targets within the unknown or quantitate the targets. The identity of the target is known since it is the complement of the probe.

While there are many methods known in the art for forming and analyzing such arrays, all of them assume that the array will be created and, subsequently analyzed or "read" in "an x, y format", where "x" and "y" are the coordinate axes of a two dimensional Cartesian coordinate system. "Reading" an array in an x, y format typically requires raster scanning a laser beam across the array surface. Typically, either the laser beam and the fluorescence detection system must be moved or the array must be moved in relation to the optics to scan in a raster pattern or x, y format. In either case, the system typically requires some kind of x, y table or a single axis motion table and a galvanometer.

Typical specifications of a biological array require a very sensitive optical assay. Therefore, the size of the laser beam is normally focussed to about 5 to 10 microns to meet the sensitivity requirements of the assay. In order to scan an array surface in increments of 5 or 10 microns, the x, y table or galvanometer must be very precise. Such precision is normally expensive. The price of an optical scanner is typically above $50,000, which can be cost prohibitive for small analytical laboratories.

Moreover, if an x, y table is employed to move either the optics or the array in a raster scan fashion, the x, y table must be moved in a precise way. In particular, the table must be moved: (i) very quickly in one direction; (ii) it must accelerate up to "reading velocity" prior to the beam touching the array; (iii) then it must move across the array at a constant speed; (iv) decelerate outside of the array area; (v) reverse direction; and then repeat steps (i)–(v) until the surface is completely scanned. A significant portion of the total time required to scan the array is spent in making changes in the direction during the raster scan.

Moreover, in the x, y format, the laser beam must be scanned beyond the region of interest on the array to allow space for the deceleration of the beam and for the beam to reverse direction. Since the array under test is normally glued into a package, the beam may hit a glue edge or line. Conventionally, adhesive glues are often fluorescent and are likely to be more fluorescent than the signals from the very sensitive array. If the laser beam encounters the glue line, the resulting signal can overload the detection system. Overload can result in either temporary degradation of the detection channel or permanent damage.

If a galvanometer is employed, the collection optics must be much larger to collect signal from the entire swept line. Larger optics are more expensive and more likely to have aberrations.

Therefore, it would be advantageous to have an assay system that does not require the complexities and expense of, and avoids the problems associated with, the traditional x, y raster scan format.

U.S. Pat. No. 5,508,200 Tiffany et al., discloses an automated chemical analysis system for high volume chemical testing that creates arrays of chemical reactions on an absorbent media or a solid substrate patterned with microwells. The system includes a dispensing mechanism for dispensing multiple reagents or test samples within a common test area on the media. The common test area has microcuvettes or microwells to hold the samples and reagents and prevent commingling of chemicals between each sample. Mixing of the samples with the reagents is either performed before dispensing or on the media. Tiffany employs a CCD camera to simultaneously monitor the individual reactions at the discrete locations within the common area.

In one embodiment, Tiffany discloses using a rotatable circular disk of an absorbent matrix instead of a continuous strip for the purpose of accommodating multiple sample spots. As a result, photometric measurements with the CCD camera can be made at a single station. The circular disk is rotated to bring the set of microcuvettes into position for photometric measurement. The circular disk format facilitates analyses requiring measurement at variable time intervals and also multipoint rate analyses because of the ease of returning to the single camera station.

However for several reasons, the chemical analysis system described by Tiffany et al. is not conducive to the conventional analysis of biological materials using arrays, as described above. The arrays of biological materials require that each feature be exposed to the entire quantity of the target sample since the concentration of the analytes is typically orders of magnitude less than that of chemistries Tiffany et al. use. The analysis system of Tiffany et al. requires fluid isolation between each location. This is achieved by physical isolation (microwells) or by using such small fluid aliquots on absorbent media that the fluid spots do not connect.

In the manufacture of conventional biological arrays, the read probes are chemically bound to the substrate and the targets are hybridized to the read probes. Tiffany et al. disclose using reagents and samples that are dried onto the absorbent media or captured within a microwell. Therefore, the system of Tiffany et al. would not be conducive to the conventional hybridization and subsequent wash steps.

Moreover, Tiffany et al. disclose using CCD cameras for optical interrogation of the individual chemical reactions. Current technology in CCD cameras is not as sensitive to fluorescent signal as a laser beam with a photomultiplier tube detector used in conventional biological array assays. The conventional biological array assay described above typically scans the entire surface in a systematic pattern rather than taking simultaneous camera shots of an entire area.

The methodologies disclosed by Tiffany et al. dictate a "dispense and immediately read" process. These methodologies are not useful to conventional biological array assays, which require reaction times of at least 30 minutes to overnight to complete. Furthermore, Tiffany et al. disclose using homogeneous chemistries in the chemical analysis system. The conventional biological array allows for heterogeneous assays.

U.S. Pat. No. 4,940,322 Miwa et al. discloses a fluorescent analysis apparatus for measuring the presence of microorganisms using fluorescent substances. Each sample is placed in a discrete container with reactive liquids. The containers are placed in a rotatable holder or carousel in a reaction section of the system. After a specified time, the containers are rotated into position by means of a motor and gearing arrangement at a measuring section of the system, where they are interrogated with a fluorescent excitation light.

The analysis apparatus disclosed by Miwa et al. is also not conducive to biological array assays for many of the same reasons mentioned above for Tiffany et al. In particular, the apparatus of Miwa et al. does not allow for conventional manufacture and hybridization processes used in conventional biological array assays.

U.S. Pat. No. 5,812,272 issued to King et al. and assigned to the assignee of the present invention, discloses an apparatus and method for analyzing target chemicals with a tiled light source array. At column 9, line 28, it is disclosed that the light source tiles can be arranged in a circular pattern and held in place by grooved channels formed within a support. However, there is no disclosure of why or how the circular pattern of tiles is used and if there are any advantages to using a circular pattern of light source tiles.

Thus, it would be advantageous to have an apparatus and method for assaying biological materials that follows much of the conventional array manufacturing and analysis methodologies, but employs a less complex interrogation scheme.

SUMMARY OF THE INVENTION

The present invention provides an apparatus, systems and methods for assaying biological materials which use an r, $\theta$ format, where "r" and "$\theta$" are the coordinate axes of a two dimensional polar coordinate system. In accordance with the present invention, the complexities and expense of conventional optical interrogation equipment and methods are overcome, without compromising assay sensitivity, precision and speed.

The apparatus of the present invention is an array of discrete features of biological material in a circular or annular array pattern. The present array is manufactured using conventional materials, manufacturing equipment and methods, except that the biological materials are deposited onto a substrate in the circular or annular array pattern.

One system of the present invention is a system for synthesizing arrays that includes a spinner assembly for rotating the apparatus during the synthesis and deposition of the biological material on the substrate to form the circular or annular pattern of biological features. The spinner assembly provides efficient means for annular deposition and spreading and removing ancillary materials used in the synthesis process.

Another system of the present invention is a system for hybridizing the array apparatus of the invention with a complementary biological material. The hybridization system uses well-established methods and materials for hybridization. However, the hybridization system further includes a spinner assembly to rotate the apparatus after the complementary biological material is added. The spinning motion spreads the complementary biological material efficiently over the annular array such that less complementary biological material is needed for the assay. Further the spinning motion effectively removes unhybridized material and ancillary materials and moves any bubbles that form out of the array area. In the systems of synthesizing and hybridizing, the spinner assemblies are used to spin the array such that the advantages of centrifugal force on array processing are realized.

Still another system of the present invention is a system for optically interrogating the apparatus of the present invention. The interrogation system includes a conventional light source to emit a light beam, optics, detection and analysis subsystems. Moreover, the interrogation system of the present invention employs a scanning assembly that holds and rotates the apparatus so that the light source and optics remain stationary, and a galvanometer is not necessary. The hybridized apparatus is scanned and read in a r, $\theta$ format using a spinner subassembly. The optical interrogation further comprises a linear stage to move the apparatus or the optics radially to efficiently expose all features in the annular array pattern on the apparatus to the light source.

The r, $\theta$ format is simpler to use and implement than the conventional x, y format. Detection of the fluorescent signals from the hybridized targets is accomplished with detection systems employing conventional photomultiplier tubes, so that sensitivity is not compromised. The signal information gathered by the conventional detection system is stored and processed by conventional analysis systems that are adapted to process r, θ formatted data and provide information about the target sample under investigation.

In accordance with the invention, the optics in the optical scanner advantageously remain focused on a single point. The array is scanned in a spiral pattern or by sweeping around a circle at a specific radius and then stepping to a next radius and sweeping in a circle again. The scan profile is scanned either with a constant angular and radial speed or with a constant rate of area scanned. The entire scan time is dedicated to reading active array rather than accelerating and decelerating after every scan line, as in the conventional x, y format. The present system requires a motor to rotate the array and a linear system to move the array radially. In another embodiment, the linear system is adapted to move the read optics instead of the array. Therefore, the present invention avoids the expense of a precision x, y table in the optical scanning equipment.

The present system allows the optics to be smaller, lower weight and less expensive. Optics with small field of view can be made with high light collection efficiency (high numerical aperture) since aberrations are more easily avoided. A "high" numerical aperture starts at approximately 0.5–0.6. The optics only need to be corrected for a field of view covering the alignment tolerances, as in conventional systems. In addition, the present system avoids using large galvanometer mirrors, which are otherwise associated with high numerical aperture scanners.

Moreover, in accordance with the invention, the present system avoids the risk of detector overload found in the optical scanners using the x, y format discussed above. The array may be packaged in some applications. Advantageously, the array is adhered using an annular glue line, rendering the glue line concentric with the scan pattern. Therefore, there is no risk of the laser beam crossing the glue line and overloading the detection system.

The present invention also includes a method for assaying biological materials. The method includes the steps of providing an array of biological material on a substrate in an annular array of discrete features, hybridizing the array with another biological material, optically interrogating the hybridized array and determining information about the biological materials from the results of the interrogation. The steps of the method use the respective systems for synthesizing, hybridizing and optically interrogating the apparatus. The method takes advantage of the use of the spinner assemblies to implement the r,θ format in accordance with the invention. Rotating and spinning the substrate in the synthesis, the hybridization and the optical interrogation of the array provide many advantages to the process of assaying biological materials that are not found in conventional systems using an x, y format The present invention provides additional advantages. For example, during the manufacture of the hybridized array apparatus, centrifugal force is applied to the fluids on the array. Quite advantageously, the centrifugal force simplifies the washing procedure after hybridization because the fluids are easily removed by spinning the substrate. Moreover, the centrifugal force advantageously minimizes the quantity of target sample required for analysis in several ways: First, the target sample is spread efficiently over the array features by the spinning motion, so that little target sample is needed for hybridization. In particular, in a preferred embodiment, the apparatus is packaged in a housing, where little target sample is needed to fill the fluid channel in the package leading to the array surface. Second, the surface energy of the package array requires less control since capillary action is not needed to fill the fluid channel in the package. Third, the filling and emptying of the fluid cavity in the package can be handled automatically. Moreover, any bubbles in the fluid, which form during the sample loading or hybridization steps, are advantageously spun out of the active read area.

BRIEF DESCRIPTION OF THE DRAWINGS

The various features and advantages of the present invention may be more readily understood with reference to the following detailed description taken in conjunction with the accompanying drawings, where like reference numerals designate like structural elements, and in which:

FIG. 3B illustrates a cross sectional view of the array housing taken along lines 3B—3B of FIG. 3A;

FIG. 3D illustrates a cross sectional view of the preferred embodiment of the array package taken along lines 3D—3D of FIG. 3A;

FIG. 8A illustrates the method of assaying biological materials; FIG. 8B illustrates the method of synthesizing the array; FIG. 8C illustrates the method of hybridizing the array with another biological material; and FIG. 8D illustrates the method of optically interrogating the hybridized array, all in accordance with the present invention.

MODES FOR CARRYING OUT THE INVENTION

Definitions

Figure 1A:
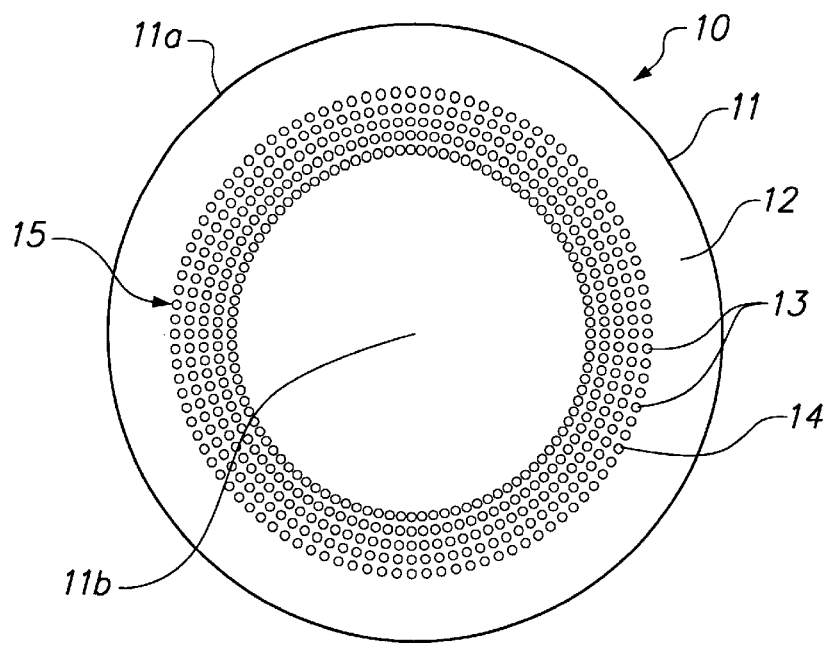
FIG. 1A illustrates a top view of one embodiment of an array apparatus according to the present invention.

The following terms are intended to have the following general meanings as they are used herein:

Polynucleotide—a compound or composition that is a polymeric nucleotide or nucleic acid polymer. The polynucleotide may be a natural compound or a synthetic compound. In the context of an assay, the polynucleotide can have from about 5 to 5,000,000 or more nucleotides. The larger polynucleotides are generally found in the natural state. In an isolated state the polynucleotide can have about 30 to 50,000 or more nucleotides, usually about 100 to 20,000 nucleotides, more frequently 500 to 10,000 nucleotides. It is thus obvious that isolation of a polynucleotide from the natural state often results in fragmentation. The polynucleotides include nucleic acids, and fragments thereof, from any source in purified or unpurified form including DNA, double-stranded or single stranded (dsDNA and ssDNA), and RNA, including t-RNA, m-RNA, r-RNA, mitochondrial DNA and RNA, chloroplast DNA and RNA, DNA/RNA hybrids, or mixtures thereof, genes, chromosomes, plasmids, the genomes of biological materials such as microorganisms, e.g. bacteria, yeasts, viruses, viroids, molds, fungi, plants, animals, humans, and the like. The polynucleotide can be only a minor fraction of a complex mixture such as a biological sample. Also included are genes, such as hemoglobin gene for sickle-cell anemia, cystic fibrosis gene, oncogenes, cDNA, and the like.

The polynucleotide can be obtained from various biological materials by procedures well known in the art. The polynucleotide, where appropriate, may be cleaved to obtain a fragment that contains a target nucleotide sequence, for example, by shearing or by treatment with a restriction endonuclease or other site specific chemical cleavage method.

For purposes of this invention, the polynucleotide, or a cleaved fragment obtained from the polynucleotide, will usually be at least partially denatured or single stranded or treated to render it denatured or single stranded. Such treatments are well known in the art and include, for instance, heat or alkali treatment, or enzymatic digestion of one strand. For example, double stranded DNA (dsDNA) can be heated at 90–100° C. for a period of about 1 to 10 minutes to produce denatured material, while RNA produced via transcription from a dsDNA template is already single stranded.

Target nucleotide sequence—a sequence of nucleotides to be identified, usually existing within a portion or all of a polynucleotide, usually a polynucleotide analyte. The identity of the target nucleotide sequence generally is known to a extent sufficient to allow preparation of various probe sequences hybridizable with the target nucleotide sequence.

The target sequence usually contains from about 30 to 5,000 or more nucleotides, preferably 50 to 1,000 nucleotides. The target nucleotide sequence is generally a fraction of a larger molecule or it may be substantially the entire molecule such as a polynucleotide as described above. The minimum number of nucleotides in the target nucleotide sequence is selected to assure that the presence of a target polynucleotide in a sample is a specific indicator of the presence of polynucleotide in a sample. The maximum number of nucleotides in the target nucleotide sequence is normally governed by several factors: the length of the polynucleotide from which it is derived, the tendency of such polynucleotide to be broken by shearing or other processes during isolation, the efficiency of any procedures required to prepare the sample for analysis (e.g. transcription of a DNA template into RNA) and the efficiency of detection and/or amplification of the target nucleotide sequence, where appropriate.

Oligonucleotide—a polynucleotide, usually single stranded, usually a synthetic polynucleotide but may be a naturally occurring polynucleotide. The oligonucleotide(s) are usually comprised of a sequence of at least 5 nucleotides, usually, 10 to 100 nucleotides, more usually, 20 to 50 nucleotides, preferably, 10 to 30 nucleotides, more preferably, 20 to 30 nucleotides, and desirably about 25 nucleotides in length.

Various techniques can be employed for preparing an oligonucleotide. Such oligonucleotides can be obtained by biological synthesis or by chemical synthesis. For short sequences (up to about 100 nucleotides), chemical synthesis will frequently be more economical as compared to the biological synthesis. In addition to economy, chemical synthesis provides a convenient way of incorporating low molecular weight compounds and/or modified bases during specific synthesis steps. Furthermore, chemical synthesis is very flexible in the choice of length and region of target polynucleotides binding sequence. The oligonucleotide can be synthesized by standard methods such as those used in commercial automated nucleic acid synthesizers. Chemical synthesis of DNA on a suitably modified glass or resin can result in DNA covalently attached to the surface. This may offer advantages in washing and sample handling. For longer sequences standard replication methods employed in molecular biology can be used such as the use of M13 for single stranded DNA as described in J. Messing (1983) Methods Enzymol. 101:20–78.

In situ synthesis of oligonucleotide or polynucleotide probes on the substrate is performed in accordance with well-known chemical processes, such as sequential addition of nucleotide phosphoramidites to surface-linked hydroxyl groups, as described by T. Brown and Dorcas J. S. Brown in *Oligonucleotides and Analogues A Practical Approach*, F. Eckstein, editor, Oxford University Press, Oxford, pp. 1–24 (1991), and incorporated herein by reference. Indirect synthesis may be performed in accordance biosynthetic techniques (e.g. polymerase chain reaction "PCR"), as described in Sambrook, J. et al., "Molecular Cloning, A Laboratory Manual", $2^{nd}$ edition 1989, incorporated herein by this reference.

Other methods of oligonucleotide synthesis include phosphotriester and phosphodiester methods (Narang, et al., (1979) Meth. Enzymol 68:90) and synthesis on a support (Beaucage, et al. (1981) Tetrahedron Letters 22:1859–1862) as well as phosphoramidate techniques (Caruthers, M. H., et al., "Methods in Enzymology," Vol. 154, pp. 287–314 (1988) and others described in "Synthesis and Applications of DNA and RNA," S. A. Narang, editor, Academic Press, New York, 1987, and the references contained therein. The chemical synthesis via a photolithographic method of spatially addressable arrays of oligonucleotides bound to glass surfaces is described by A. C. Pease, et al., Proc. Nat. Aca. Sci. USA (1994) 91:5022–5026, all incorporated herein by reference.

Oligonucleotide probe—an oligonucleotide employed to bind to a portion of a polynucleotide such as another oligonucleotide or a target nucleotide sequence. The design and preparation of the oligonucleotide probes are generally dependent upon the sensitivity and specificity required, the sequence of the target polynucleotide and, in certain cases, the biological significance of certain portions of the target polynucleotide sequence.

Monomer—A member of the set of small molecules which can be joined together to form a polymer. The set of monomers includes but is not restricted to, for example, the set of common L-amino acids, the set of D-amino acids, the set of synthetic amino acids, the set of nucleotides and the set of pentoses and hexoses. As used herein, monomers refers to any member of a basis set for synthesis of a polymer. For example, dimers of the 20 naturally occurring L-amino acids form a basis set of 400 monomers for synthesis of polypeptides. Different basis sets of monomers may be used at successive steps in the synthesis of a polymer. Furthermore, each of the sets may include protected members that are modified after synthesis.

Nucleotide—a base-sugar—phosphate combination that is the monomeric unit of nucleic acid polymers, i.e., DNA and RNA.

Hybridization (hybridizing) and binding—in the context of nucleotide sequences these terms are used interchangeably herein. The ability of two nucleotide sequences to hybridize with each other is based on the degree of complementarity of the two nucleotide sequences, which in turn is based on the fraction of matched complementary nucleotide pairs. The more nucleotides in a given sequence that are complementary to another sequence, the more stringent the conditions can be for hybridization and the more specific will be the binding of the two sequences. Increased stringency is achieved by elevating the temperature, increasing the ratio of co-solvents, lowering the salt concentration, and the like.

In accordance with the invention, the conventional hybridization solutions and processes for hybridization can be used, such as those described in J. Sambrook, E. F. Fritsch, T. Maniatis, *Molecular Cloning: A Laboratory Manual*, Cold Spring Harbor Laboratory Press, Cold Spring Harbor, Ed. $2^{nd}$, 1989, vol. 1–3, incorporated herein by reference. Conditions for hybridization typically include (1) high ionic strength solution, (2) at a controlled temperature, and (3) in the presence of carrier DNA and detergents and divalent cation chelators, all of which are well known in the art.

Hybridization efficiency—the productivity of a hybridization reaction measured as either the absolute or relative yield of oligonucleotide probe/polynucleotide target duplex formed under a given set of conditions in a given amount of time.

Complementary—Two sequences are complementary when the sequence of one can bind to the sequence of the other in an anti-parallel sense wherein the 3'-end of each sequence binds to the 5'-end of the other sequence and each A, T(U), G, and C of one sequence is then aligned with a T(U), A, C, and G, respectively, of the other sequence. RNA sequences can also include complementary G=U or U=G base pairs.

Substrate or surface—a porous or non-porous water insoluble material. The surface can have any one of a number of shapes, such as strip, plate, disk, rod, particle, including bead, and the like. The substrate can be hydrophobic or hydrophilic or capable of being rendered hydrophobic or hydrophilic and includes inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly (4-methylbutene), polystyrene, polymethacrylate, poly(ethylene terephthalate), nylon, poly (vinyl butyrate), etc.; either used by themselves or in conjunction with other materials; glass available as Bioglass, ceramics, metals, and the like. Natural or synthetic assemblies such as liposomes, phospholipid vesicles, and cells can also be employed. Common substrates used for arrays are surface-derivatized glass or silica, or polymer membrane surfaces, as described in Z. Guo et al. (cited above) and U. Maskos, E. M. Southern, *Nucleic Acids Res* 20, 1679–84 (1992) and E. M. Southern et al., *Nucleic Acids Res* 22, 1368–73 (1994), both incorporated herein by reference.

Immobilization of oligonucleotides on a substrate or surface may be accomplished by well-known techniques, commonly available in the literature. See, for example, A. C. Pease, et al., *Proc. Nat. Acad. Sci. USA,* 91:5022–5026 (1994); Z. Guo, R. A. Guilfoyle, A. J. Thiel, R. Wang, L. M. Smith, *Nucleic Acids Res* 22, 5456–65 (1994); and M. Schena, D. Shalon, R. W. Davis, P. O. Brown, *Science,* 270, 467–70 (1995), each incorporated herein by reference.

Label—a member of a signal producing system. Usually the label is part of a target nucleotide sequence or an oligonucleotide probe, either being conjugated thereto or otherwise bound thereto or associated therewith. The label is capable of being detected directly or indirectly. Labels include (i) reporter molecules that can be detected directly by virtue of generating a signal, (ii) specific binding pair members that may be detected indirectly by subsequent binding to a cognate that contains a reporter molecule, (iii) oligonucleotide primers that can provide a template for amplification or ligation or (iv) a specific polynucleotide sequence or recognition sequence that can act as a ligand such as for a repressor protein, wherein in the latter two instances the oligonucleotide primer or repressor protein will have, or be capable of having, a reporter molecule. In general, any reporter molecule that is detectable can be used.

The reporter molecule can be isotopic or nonisotopic, usually non-isotopic, and can be a catalyst, such as an enzyme, a polynucleotide coding for a catalyst, promoter, dye, fluorescent molecule, chemiluminescer, coenzyme, enzyme substrate, radioactive group, a small organic molecule, amplifiable polynucleotide sequence, a particle such as latex or carbon particle, metal sol, crystallite, liposome, cell, etc., which may or may not be further labeled with a dye, catalyst or other detectable group, and the like. The reporter molecule can be a fluorescent group such as fluorescein, a chemiluminescent group such as luminol, a terbium chelator such as N-(hydroxyethyl) ethylenediaminetriacetic acid that is capable of detection by delayed fluorescence, and the like.

The label can generate a detectable signal either alone or together with other members of the signal producing system. As mentioned above, a reporter molecule can be bound directly to a nucleotide sequence or can become bound thereto by being bound to an specific binding pair (sbp) member complementary to an sbp member that is bound to a nucleotide sequence. Examples of particular labels or reporter molecules and their detection can be found in U.S. Pat. No. 5,508,178, the relevant disclosure of which is incorporated herein by reference. When a reporter molecule is not conjugated to a nucleotide sequence, the reporter molecule may be bound to an sbp member complementary to an sbp member that is bound to or part of a nucleotide sequence.

Signal producing system—the signal producing system may have one or more components, at least one component being the label. The signal producing system generates a signal that typically relates to the presence or amount of a target polynucleotide in a medium. The signal producing system includes all of the reagents required to produce a measurable signal. Other components of the signal producing system may be included in the developer solution and can include substrates, enhancers, activators, chemiluminescent compounds, cofactors, inhibitors, scavengers, metal ions, specific binding substances required for binding of signal generating substances, and the like. Other components of the signal producing system may be coenzymes, substances that react with enzymic products, other enzymes and catalysts, and the like. The signal producing system provides a signal detectable by external means, by use of electromagnetic radiation, desirably by visual examination. Signal-producing systems that may be employed in the present invention are those described more fully in U.S. Pat. No. 5,508,178, the relevant disclosure of which is incorporated herein by reference.

Ancillary materials—Various ancillary materials will frequently be employed in the methods and assays utilizing biological materials designed in accordance with the present invention. For example, conventional ancillary materials, such as reagents and wash fluids for the synthesis and hybridization of biological materials, including but not limited to acetonitrile, buffers and salts, will normally be used in an assay medium, as well as stabilizers for the assay medium and the assay components. Frequently, in addition to these additives, ancillary materials include but are not limited to proteins, such as albumins, organic solvents, such as formamide, quaternary ammonium salts, polycations, such as spermine, surfactants, particularly non-ionic surfactants, binding enhancers, e.g., polyalkylene glycols, or the like.

Biological material—nucleic acids, such as polynucleotides, oligonucleotides, oligonucleotide probes, target nucleotide sequences, proteins, amino acids, antibodies, antigens, enzymes, coenzymes, ligands, receptors, hormones and labels, and monomers thereof, and genes that specify any of the above, and any other materials from any form of life.

Member of a specific binding pair ("sbp member")—one of two different molecules, having an area on the surface or in a cavity that specifically binds to and is thereby defined as complementary with a particular spatial and polar organization of the other molecule. The members of the specific binding pair are referred to as cognates or as ligand and receptor (antiligand). These may be members of an immunological pair such as antigen-antibody, or may be operator-repressor, nuclease-nucleotide, biotin-avidin, hormones-hormone receptors, nucleic acid duplexes, IgG-protein A, DNA-DNA, DNA-RNA, and the like.

Detailed Description of the Invention

The apparatus 10 of the present invention comprises a substrate 11 having a surface 12 and biological material 13, either a biological probe 13a or a target sample 13b, bound in an annular region on the surface 12 of the substrate in the form of discrete features 14. In the preferred embodiment, the biological probes 13a are bound to the substrate surface 12. The features 14 may be patterned in the annular region on the substrate 11 in any number of annular patterns. Figures 1A and 1C–1F illustrate examples of five different potential array patterns realized by the invention. FIG. 1A illustrates one embodiment of the array apparatus 10 of the present invention. In this embodiment, the array 10 includes a substrate 11, which is preferably circular in shape, and has an array pattern comprised of a plurality of annular rings positioned in concentric circles 15, the outermost ring 15a being positioned adjacent to the edge 11a of the substrate and having the largest diameter, wherein the concentric rings 15 decrease in diameter as they approach the center 11b of the substrate 11.

Figure 1B:
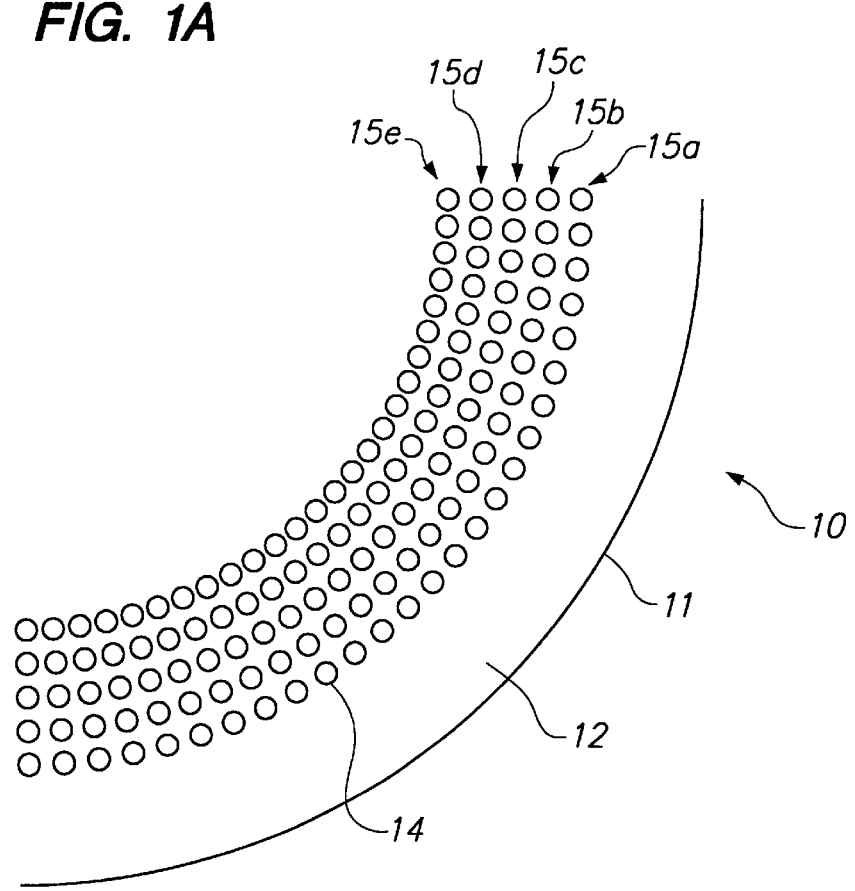
FIG. 1B illustrates a magnified view of a portion of the array in FIG. 1A according to the present invention.

FIG. 1B is a magnified view of the deposits of biological material 13 as discrete features 14 on the substrate 11, which better illustrates a portion of each concentric ring 15a–15e of the preferred embodiment in FIG. 1A, and the spacing between features 14 and rings 15. The discrete features 14 within each ring 15 are spaced apart by approximately 30–200 microns, and preferably at least approximately 50 microns, in order to ensure separation of the features 14 during deposition. The concentric rings 15 are spaced apart by approximately 30–200 microns, and preferably at least approximately 50 microns, in order to ensure separation of the features 14 in each ring 15. There are typically 5–50 concentric rings 15 in each array 10 and preferably, 20 rings 15 of discrete features 14 are used.

Figure 1C:
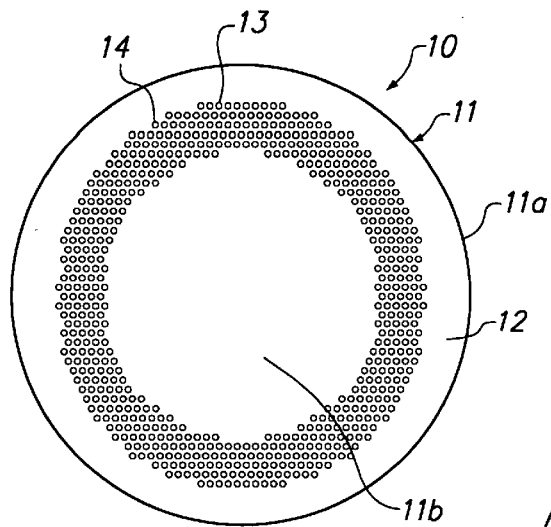
FIG. 1C–1F illustrate top views of other embodiments of the array apparatus according to the present invention.
Figure 1D:
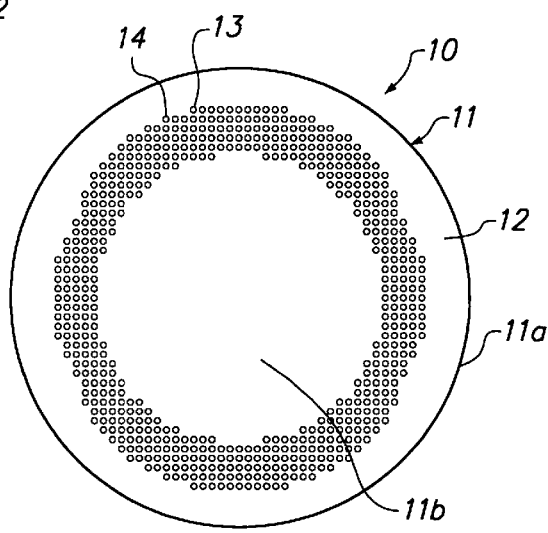
Figure 1E:
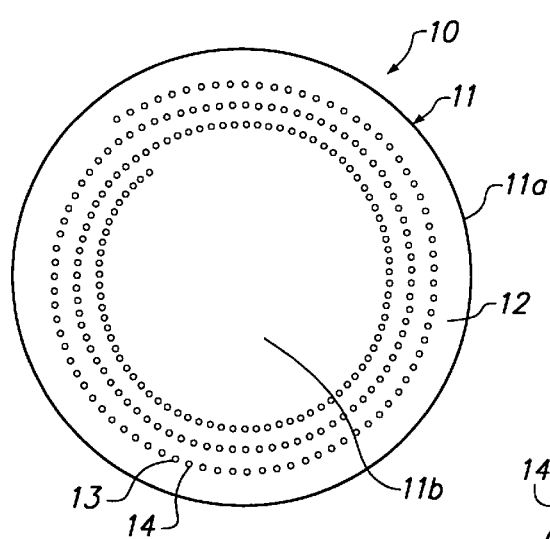
Figure 1F:
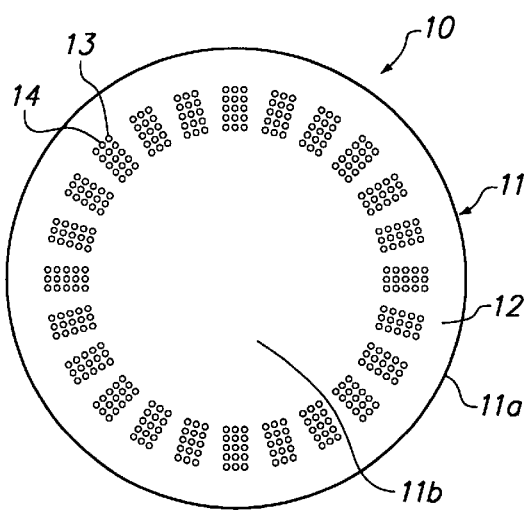

FIGS. 1C–1F illustrate examples of alternative annular array patterns that are within the scope of the invention. FIG. 1C represents an annular array pattern of features 14 arranged in ordered rows such that the features are close packed. FIG. 1D represents an annular array pattern of features 14 arranged in ordered rows and columns. There is also a lack of features 14 in particular locations in each row and column, respectively, thereby providing the distinctive annular array patterns. FIG. 1E illustrates a spiral pattern of features 14 in the annular region of the substrate. In figure 1F, the features 14 are patterned in segmented annular rings. FIG. 1F illustrates segments containing three columns of six features 14 each. The feature 14 locations on the left side of each array pattern in figures 1C, 1C and 1F are mirror images of the feature locations on the right side of the array pattern. It should be noted that FIGS. 1A, 1C–1F are merely illustrative and not intended to limit the scope of the invention. As long as the pattern is located in an annular region of the substrate, or has an annular array pattern, it is within the scope of the invention. It should also be noted that although a circular substrate is illustrated in Figures 1A–1F, substrates that are substantially elliptical, rectangular, square, or other shapes are within the scope of the present invention.

In accordance with the invention, the substrates are made of glass, fused silica or clear plastics, and preferably water white glass is used in the invention because of its low intrinsic fluorescence. The water white glass can be obtained from Erie Scientific or Corning.

The processes and materials used for the manufacture of the array apparatus 10 will depend on the biological material that will be analyzed. For the purposes of simplifying the discussion, hereinafter the present invention will be described with respect to analysis of nucleic acids, polynucleotides, oligonucleotides or nucleotides, and the like, and the biological material 13 bound to the substrate 11 will hereinafter be referred to as the probes 13a, or oligonucleotide probes 13a. The biological material introduced for hybridization shall be referred to as the target sample 13b or target nucleotide sequences 13b. The target samples 13b will be labeled with a signal producing system, such as a fluorophore label, which will fluoresce when illuminated. It is not the intent of the inventors to be limited to this particular class of biological materials for application of the invention; to the surface-bound "probe" configuration; or to the target sample 13b having the signal producing system. It should be understood by those skilled in the art that the present invention has broad application to biological material analysis and that the present apparatus 10 is configurable to accommodate either member of complementary biological materials under evaluation as the surface bound material and that either the probes or the targets may contain the signal producing system. For information regarding the processes and materials used for the manufacture of arrays of biological materials, such as proteins, antibodies, or the like in accordance with the invention, see for example U.S. Pat. Nos. 4,591,570; 5,143,854; and 5,252,743 and the following articles: Ekins, R. et. al., "Development of microspot multi-analyte ratiometric immunoassay using dual fluorescent-labeled antibodies" *Analytica Chimica Acta*, (1989), 227:73–96; and Ekins, RP and FW Chu. "Multianalyte microspot immunoassay—microanalytical 'compact disc' of the future" (1991).

In accordance with the invention, the oligonucleotide probes 13a are either synthesized directly onto the substrate 11 (in situ) using conventional chemical processes or synthesized indirectly using biological processes and deposited onto the substrate 11. In the preferred embodiment, the oligonucleotide probes 13a are synthesized in-situ using the conventional methods referenced above.

The present invention applies nucleotide bases to the array substrate 11 using the technology concepts from the thermal ink jet printing systems made by Hewlett-Packard of Palo Alto, Calif., or piezoelectric printing systems, made by Epson of Japan. According to a preferred embodiment, in situ synthesis of oligonucleotide probes 13a is accomplished with a thermal ink jet array writer 20 illustrated in FIG. 2. The array writer 20 of the present invention is an automated system that is computer controlled and comprises an enclosure 21, a stage 22 for holding substrate 11 while probes 13a are synthesized on the surface 12 of the substrate 11, and a spinner assembly 23 for spinning the stage 22.

The stage 22 is removably attached to the spinning assembly 23. The stage 22 comprises a top plate 22a and a pedestal portion 22b. The top plate 22a has a recess 22c machined into one surface for receiving the array substrate 11. The array substrate 11 is held in place in the recess 22c either with a clamping mechanism 22e or the stage 22 is plumbed for vacuum to hold the substrate 11 (not shown). The pedestal portion 22b of the stage 22 has a receptacle 22d.

The enclosure 21 comprises a bottom portion 21a, a wall portion 21b and a drain 24 and an orifice 25 in a bottom portion 21a of the enclosure 21. The orifice 25 is preferably centered in the middle of the bottom portion 21a. The drain 24 may be placed adjacent to the wall portion 21b of the enclosure 21.

The spinner assembly 23 comprises a rotating rod or spindle portion 26 that fits through the orifice 25 and is received by the receptacle 22d in the pedestal portion 22b of stage 22 and a motor 23a with a variable rotational speed control. When the spinning motor 23a is activated, the rotating rod 26 rotates the stage 22 incrementally and/or continuously 360 degrees. The spinner assembly 23 is a commercially available assembly available from Compumotor Div. of Parker Hannifin, Rohnert Park, Calif., for example. In the preferred embodiment, a Model No. ZETA67-51 Compumotor spinner assembly 23 was used.

Figure 2:
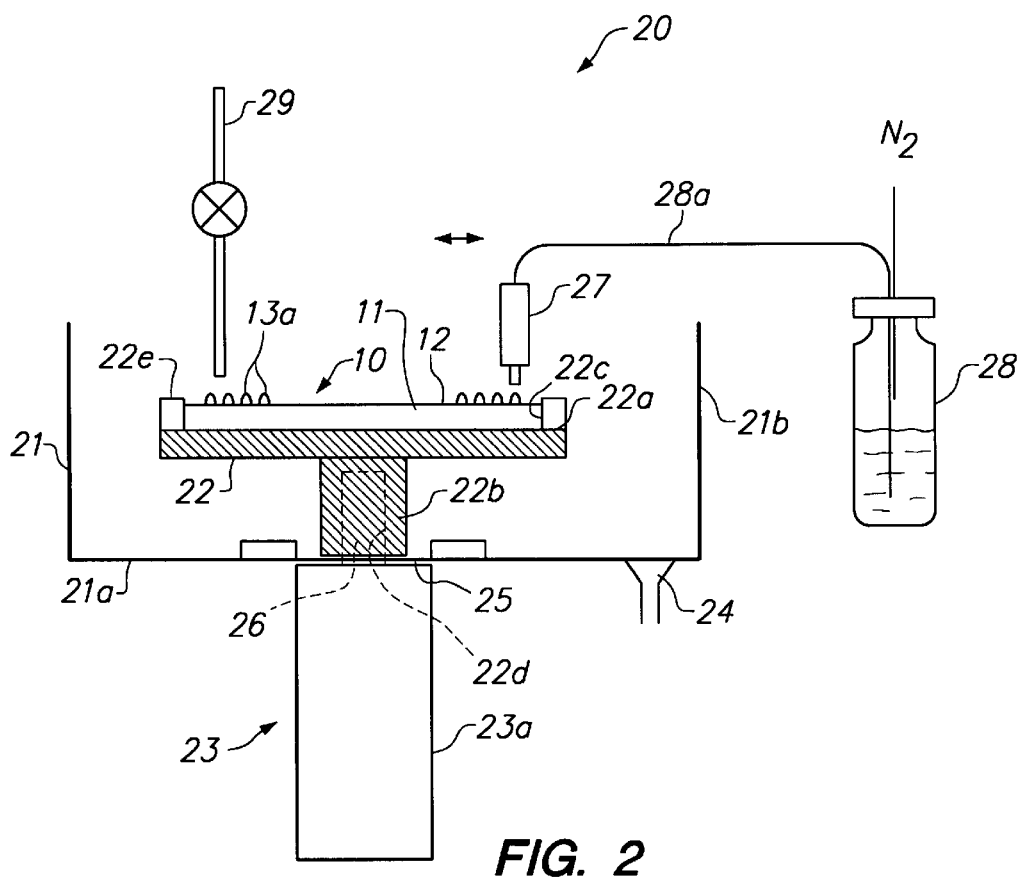
FIG. 2 illustrates a schematic view of the array synthesizer in accordance with the present invention.

The array writer 20 further comprises a plurality of ink jet heads 27. The ink jet heads 27 are each connected via tubing 28a to a separate reservoir 28 containing a different one of the four nucleotide bases and a respective conventional activator solution. Only one of each of the inkjet heads 27, reservoirs 28 and connector tubing 28a is illustrated in FIG. 2 for simplicity. The ink jet heads 27 deposit nucleotide bases in the form of droplets of biological material 13 into each feature 14 location on to the surface 12 of the substrate 11 to form probes 13a. The nucleotide base droplets 13 are placed accurately and repeatably on the feature locations 14 and such that the nucleotide base make up of probes 13a in each location 14 is known because it is preprogrammed into the computer (not shown). The spinner motor 23 rotates the substrate 11 incrementally during the printing of the nucleotide bases 13 to form the annular pattern of droplets 14 on the surface 12.

Figure 2B:
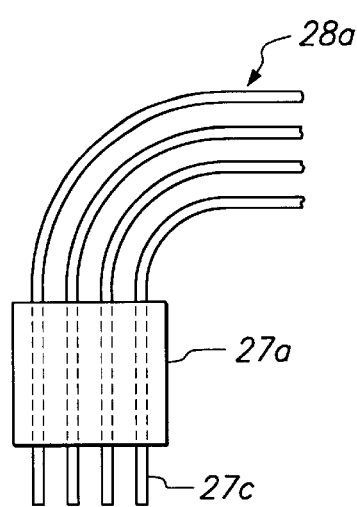
FIG. 2B and 2C illustrate side views of two embodiments of the deposition tool used in the array synthesizer of FIG. 2.

In one embodiment, four inkjet heads 27a, one for each nucleotide base type, or alternatively, a single inkjet head 27a with four nozzles 27c and four reservoirs 28, one for each nucleotide base type, may be used, as illustrated in FIG. 2B. The inkjet head 27a moves radially, while the substrate is rotated, to place the appropriate nucleotide base in the appropriate location in the annular pattern in accordance with the preprogrammed nucleotide base make-up of the probes 13a. A linear movement assembly is necessary to move the inkjet heads 27a radially across the substrate 11. For the invention, a linear assembly created using a THK Co., Inc. (Japan) linear ball slide and a generic rack and pinion motor was used. The substrate is rotated incrementally through 360 degrees during the printing process.

Figure 2C:
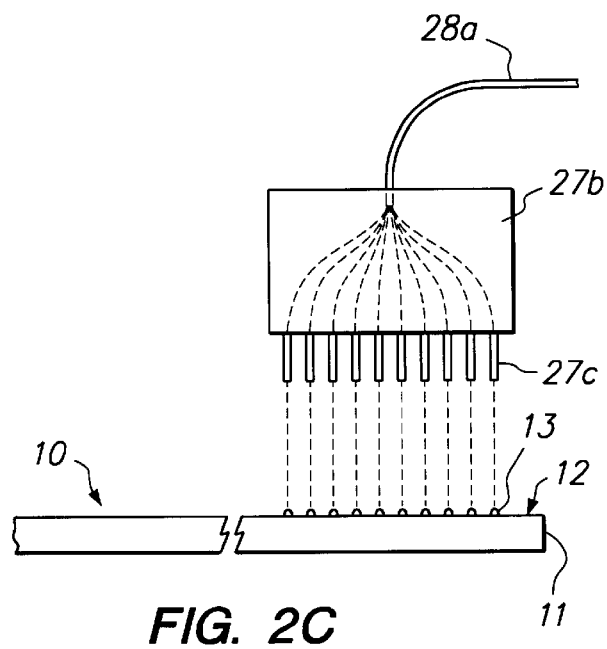

In another embodiment, each inkjet head or pen 27b has a plurality of nozzles arranged in a straight line along the radius of the circular substrate 11. Each nozzle 27c provides monomer to a location in the annular pattern on the surface 12 of the substrate 11. FIG. 2C illustrates the annular pattern of FIG. 1A, for example. There is one nozzle for each concentric annular ring 15 in each inkjet pen 27b located at the appropriate radius of the respective annular ring 15. There are four of the above described inkjet pens 27b and four reservoirs 28, one for each nucleotide base type. Each of the four inkjet heads 27b is located at a different angle, but all have their series of nozzles aligned with the same concentric rings 15. A nucleotide base may be printed onto the substrate surface 12 from a particular nozzle on a particular inkjet head 27b in accordance with the preprogrammed nucleotide base make up of the probes 13a. In this embodiment, no radially movement of the inkjet heads 27b is needed to place a nucleotide base in the proper location on the substrate 11. Only the substrate moves, in accordance with the invention, by rotating incrementally 360 degrees.

The array writer 20 further comprises a plurality of reagent/wash dispensers 29 to provide conventional ancillary materials, such as reagents and washing fluids, during the synthesis of the array 10 of the oligonucleotide probes 13a. Only one dispenser 29 is illustrated in FIG. 2 for simplicity. Four wash fluids are typically used during in situ synthesis, one for each of the conventional capping, oxidizing, deblocking and washing steps. The dispensers 29 are essentially stationary in the writer 20 and positioned above the surface 12 of the substrate 11. When the reagents or wash solutions are dispensed during the synthesis process, the spinner motor 23 rotates the stage 22 and the array substrate 11 so that the solutions are dispensed completely over the substrate surface 12. The reagents or wash solutions are removed from the surface 12 of the substrate 11 by spinning the substrate 11 at high speed within the enclosure 21. Excess reagents or wash solutions are drained from the enclosure 21 via drain 24.

Figure 8A:
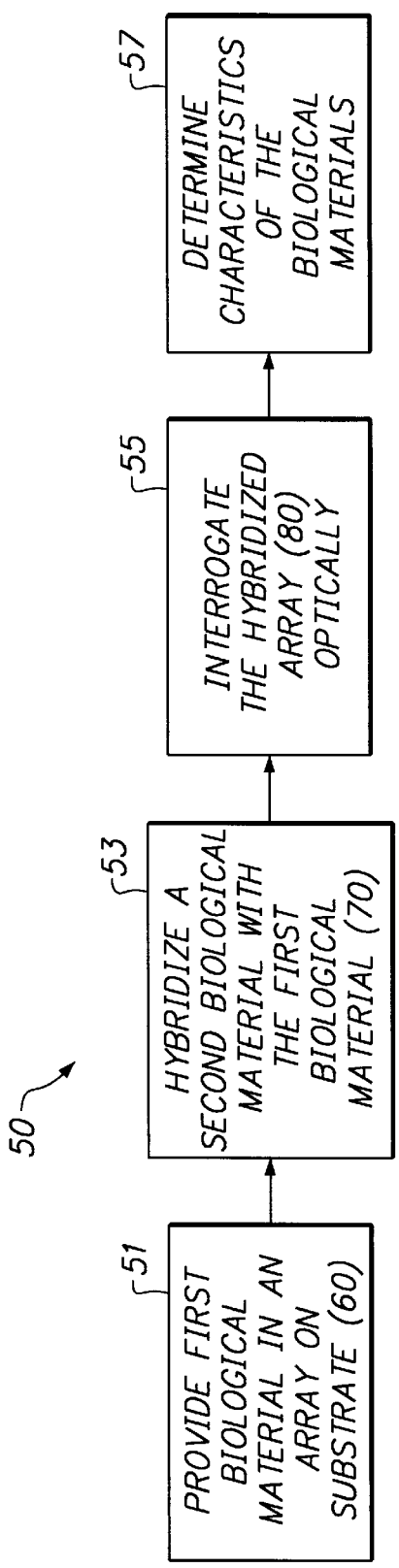
FIGS. 8A–8D illustrate flow charts of the methods of the present invention.

In the conventional in situ synthesis, the surface 12 of tie substrate 11 is prepared chemically, according to conventional methods, to receive and bind a phosphoramidite (i.e., a single nucleotide base). Referring to FIG. 8B, the method 60 of in situ synthesis using the array writer 20 in accordance with the present invention include depositing (step 61) a nucleotide base onto the prepared substrate 11 in a feature location 14 in the annular region or in an annular pattern and rotating (step 62) the substrate 12 incrementally to a next feature location 14 for deposition. The deposition and rotation steps are repeated (step 63) until all feature locations 14 in the annular pattern have a nucleotide base deposited thereon.

The bases bind to the array surface 12, but not to each other since the second binding site on each phosphoramidite has been blocked by a dimethoxytrityl. The array surface 12 is washed (step 64a) with acetonitrile solvent or equivalent from dispensers 29, as described in the literature, and then the substrate is spun (step 66a) at high speed to remove the solvent. A capping reagent is then dispensed (step 65) from dispenser 29 and flooded across the array substrate 11. In the preferred embodiment, the binding sites that did not bind a phosphoramidite are capped off rather than allow the sites to bind to another base at the next step to improve synthesis efficiency. The capping reagents are spun off (step 66b) the substrate 11 at a high speed. The substrate 12 is then washed (step 64b) in with conventional solutions of ancillary materials, as described in the literature, and then spun (step 66c) at high speed to remove the washing fluids. After the washing and spin steps 64b, 66c, an oxidizing reagent is dispensed (step 67) from dispenser 29 and flooded over the array substrate surface 12. The oxidizing reagent stabilizes the oxidation state of the phosphorous group of the newly attached base. The oxidizing reagent is spun off (step 66d) the substrate 11 at high speed. The substrate 12 is then washed (step 64c) in with conventional solutions, as described in the literature, and then spun (step 66e) at high speed to remove the wash fluids. Lastly, the dimethoxytrityl is removed according to conventional methods with deblocking reagents in a deblocking step (step 68) so that the base addition cycle can be repeated. The substrate is then spun (step 66f) at high speed to remove the deblocking reagent. The substrate 11 is then washed (step 64d) in with conventional solutions, as described in the literature, and then spun (step 66g) at high speed before the synthesis cycle (steps 61, 62, 63, 64a–64d and 65, 66a–66g, 67 and 68) is repeated and the next base is added.

The array 10 and array writer 20 of the present invention provide efficient deposition of the phosphoramidites. Each of the ink jets 27 can rapidly address all locations on the substrate 11 and avoids the complex x, y movement found in the conventional systems. Ink jet assemblies 27 with multiple nozzles eliminate any ink jet pen movement. The alignment of the nozzles in the pen assemblies 27 is permanent. The deposition of nucleotide bases 13 is continuous and without changes in direction, as in the conventional x, y format.

The spin steps (66a–66g) provide efficient washing between nucleotide base additions. In the washing steps 64a–64d, 66a–66g, the reagents are rapidly and cleanly removed without loss of substrate alignment. Advantageously, "carryover" typically found in the conventional methods of in situ synthesis, which could block the action of a chemical during synthesis, is negligible in the present invention. Moreover, the surface 12 of the substrate 11 is essentially dry before the next reagent is added.

The array 10 and array writer 20 of the present invention advantageously facilitates rapid manufacturing of custom arrays. The array writer 20 supports customer's needs for "experiment on demand" research. The specific information needed to synthesize a custom array is captured in an electronic file. The array writer 20 of the present invention reads the electronic file. A customer can order a single array and pay only for the costs of running the array writer 20 for the time needed to synthesize the single array. There are no tooling requirements or minimum lot size requirements, as is found in the conventional synthesis equipment using the x, y format.

In the conventional photolithographic methods of synthesizing arrays, the steps of deblocking, for example, require very expensive masks for each step. Approximately 80 masks are needed to make an array of oligonucleotides having 20 bases in length in the conventional photolithographic synthesis method. Therefore, the cost of making a custom array by photolithographic methods for a customer is typically prohibitive.

In the conventional pre-synthesized oligonucleotide method of forming arrays, the oligonucleotides, typically 1000 of them, are deposited onto the surface of the array substrate sequentially. This deposition process requires a potentially large production line and the arrays are typically manufactured in large quantities to minimize cost. Therefore, this method is not conducive to providing custom arrays in small quantities. However, the present invention not only can provide economically feasible custom arrays, but also can provide the custom arrays in an economically affordable lot size as small as one array.

Printing pre-synthesized (cDNAs) or oligonucleotide probes 13a in an annular region on the substrate 11 may be performed using a thermal inkjet printing system, as mentioned above. However, an oligonucleotide probe 13a at a particular location must be printed on each substrate in the manufacturing run independently of another probe 13a being printed. This may be more time consuming. Therefore, it is preferred that several substrates 11 are manufactured with pre-synthesized (cDNAs) or oligonucleotide probes 13a in a single production run in accordance with the present invention.

Figure 3A:
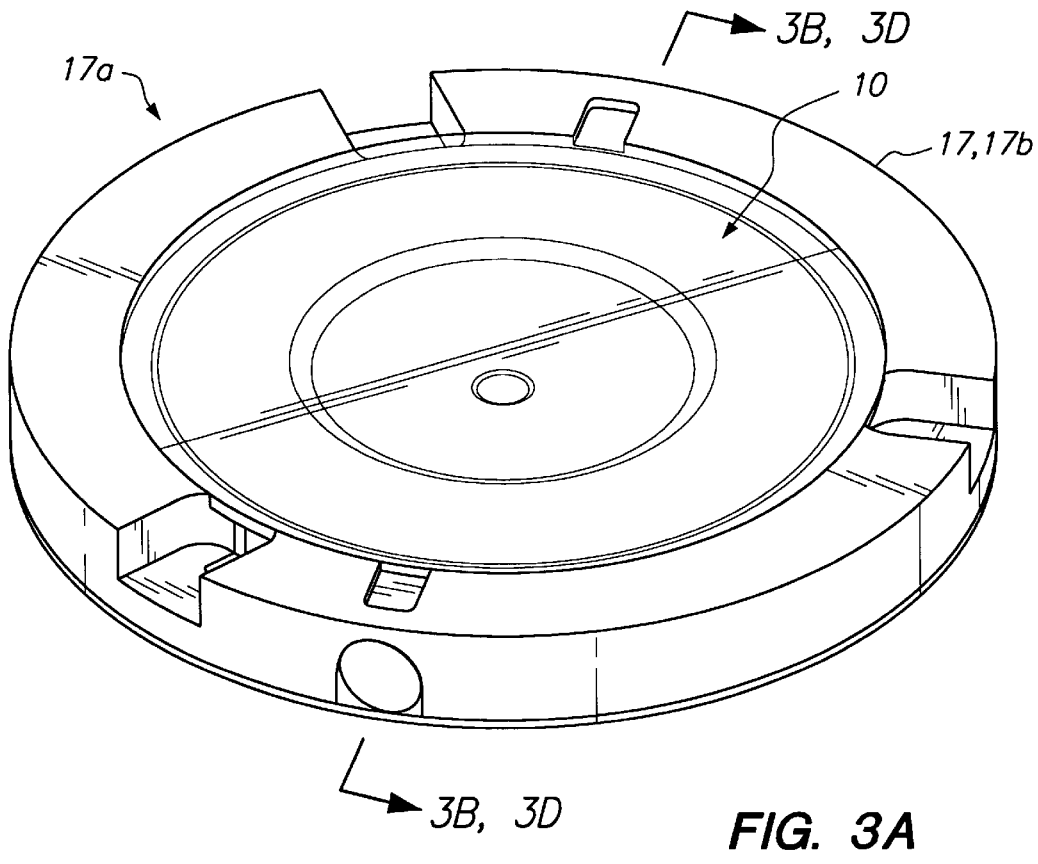
FIG. 3A illustrates a perspective view of a housing in accordance with a preferred embodiment, for holding the array of the present invention.
Figure 3C:
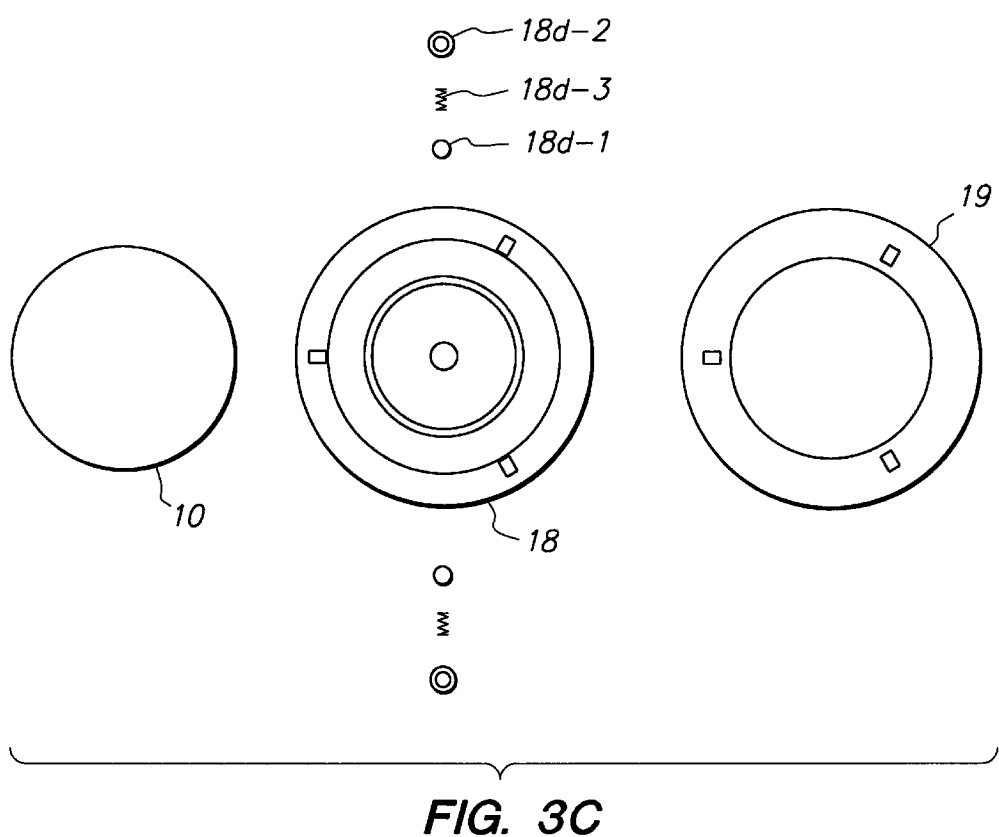
FIG. 3C illustrates an exploded view of the array and a preferred embodiment of the housing assembly in FIG. 3D.

The array 10 may or may not be packaged for handling and processing in accordance with the invention after the synthesis of the oligonucleotide probes 13a on the surface 12. In the preferred embodiment, the array 10 is packaged in a custom tooled carbon black loaded polypropylene or ABS black plastic housing 17, which can be injection molded by most injection molding companies. The packaged array of the preferred embodiment is designated hereinafter as 17a. FIG. 3A illustrates a perspective top view of the array 10 in a housing 17, 17b according to the preferred embodiment. FIG. 3B illustrates a cross sectional view of the array 10 in one embodiment of the housing 17 assembly of FIG. 3A. FIG. 3C illustrates an exploded view of the array 10 and a preferred embodiment of the housing 17b assembly, which is further illustrated in cross-sectional view in FIG. 3D.

Referring to FIGS. 3A–3D, the housing 17, 17b comprises a base portion 18. The base portion 18 has a first annular recess 18a-1 on a first side 18g where the array 10 is inserted. The base portion 18 has a second annular recess 18a-2, positioned coaxially within the first annular recess 18a-1. The second annular recess 18a-2 is shallower than the first annular recess 18a-1. The base portion has third recess 18a, positioned coaxially and preferably centered within the second annular recess 18a-2 and the first recess 18a-1. The third recess 18a is preferably circular and deeper than each of the first and second annular recesses 18a-1 and 18a-2. The third recess 18a is in at least fluid communication with at least the second annular recess 18a-2.

The base portion 18 further includes a first radially extending recess 18f-1. The first radial recess 18f-1 is in at least fluid communication with second annular recess 18a-2 and therefore, third recess 18a via pathway 18a-4. The first radial recess 18f-1 extends radially inward from the outer periphery 18e of the base portion 18.

The base portion 18 further comprises a valve mechanism 18d within first radial recesses 18f-1, or valve chamber 18f-1. The valve mechanism 18d comprises an actuator means 18d-1, a valve chamber cap 18d-2 and a biasing means 18d-3 located between actuator 18d-1 and cap 18d-2. The actuator means 18d-1 and biasing means 18d-3 are assembled into the first valve chamber 18f-1. The valve chamber cap 18d-2 is then attached to the housing 17, preferably by ultrasonic welding. In the embodiment of housing 17 illustrated in FIG. 3B, the valve chamber cap 18d-2 has a through hole to allow the fluids to exit the package via the valve chamber 18f-1 when the valve is open. The valve mechanism 18d provides a controlled means for at least fluids to exit the housing 17 via pathway 18a-4. The valve mechanism 18d is controlled by centrifugal force and is further described in U.S. patent application Ser. No. 09/133,102, filed Aug. 12, 1998, and issued Dec. 19, 2000 as U.S. Pat. No. 6,162,400, which is assigned to the assignee of the present invention, and incorporated herein in its entirety by reference.

In the preferred embodiment of the housing 17b illustrated in FIGS. 3C–3D, the base portion further comprises a second radially extending recess or valve chamber 18f-2 which is located preferably diametrically opposite from the first valve chamber 18f-1. The second valve chamber 18f-2 holds a second valve mechanism 18d similar to the first mechanism. The second valve mechanism is assembled in the second valve chamber 18f-2 in the same manner as described above for housing 17 in FIG. 3B. The housing 17b further comprises an annular frame 19 and a fourth annular recess 18a-3 on a second side 18h of the base portion 18 opposite to the first side 18g. The fourth annular recess 18a-3 is preferably deeper and narrower th the first annular recess and the second annular recess 18a-1 and 18a-2 and is located near the periphery 18e of the base portion 18. The frame 19 is attached to the second side 18h of the base portion 18, preferably by ultrasonic welding using conventional methods, thereby enclosing the fourth annular recess 18a-3 as a waste cavity 18a-3. The waste cavity 18a-3 intersects with the first valve chamber 18f-1 and the second valve chamber 18f-2, thereby providing at least fluid communication between first and second valve chambers 18f-1 and 18f-2. In this embodiment of the housing 17b, the valve caps 18d-2 do not have through holes for fluid to escape. Instead, at least one valve mechanism 18d provides a controlled means for venting the annular waste cavity 18a-3 of air via a pathway 18f-3 to the exterior of the housing 17b adjacent to the second side 18h of base portion 18. The air is vented to allow fluids to enter the waste cavity 18a-3. The valve mechanisms 18d are controlled by centrifugal force.

In both embodiments of the housing 17, 17b illustrated in FIGS. 3A—3D, the base portion 18 further comprises a fluid introduction port 18a–5 and a septum or diaphragm 18c located substantially in the center of the circular recess 18a of base portion 18. The septum 18c is captured within the fluid introduction port 18a–5 with a cover (not shown) that is ultrasonically welded into place, preferably after the base portion 18 (and frame 19, in the preferred embodiment) are attached. The fluid introduction port 18a–5 provides a passageway for the target sample 13b and other ancillary materials to be introduced into housing 17, 17b after the array 10 is attached. The septum 18c functions to allow fluids into the housing 17, 17b but prevents the fluids from escaping. The septum 18c can be made of any type of rubber.

After the housing 17, 17b is assembled, the array 10 is inserted into first annular recess 18a-1 of housing 17, 17b with the array surface 12 adjacent to second annular recess 18a-2 of base portion 18 in accordance with the preferred embodiment of the invention. The array 10 is bonded into place using conventional adhesives and the adhesive manufacturer's recommended bonding procedures. The bonded array 10 and the base portion 18 form an assay chamber 18b within the third recess 18a and second annular recess 18a-2 regions. The array surface 12 of the array 10 faces into the assay chamber 18b adjacent the second annular region 18a-2. The second annular cavity region 18a-2 is preferably from approximately 25 to 50 microns in depth.

In order to perform gene analyses, the array 10, containing oligonucleotide probes 13a, is placed in a hybridization chamber where the probes 13a are exposed to a solution of the target nucleotide sequences 13b under controlled conditions for hybridization to occur. The target sample 13b is expected to have complementary nucleotide sequences to the probe nucleotides 13a. In accordance with the invention, the conventional hybridization solutions and processes for hybridization can be used, such as those referenced above.

However, in accordance with the invention, the hybridization chamber is adapted with a pedestal shaped stage similar to the stage 22 in the array writer 20 and a spinner assembly, similar to the assembly 23 in the array writer 20 (see FIG. 2). In the preferred embodiment, the pedestal shaped stage holds the housing 17, 17b, which houses the array 10, as described above (the packaged array 17a) and therefore, the hybridization chamber or enclosure is not needed.

Figure 8C:
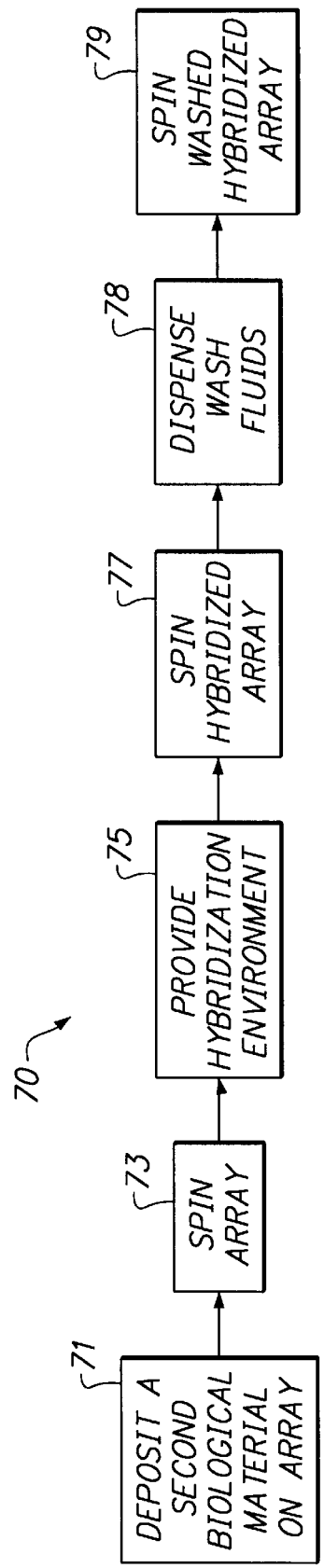
Figure 8B:
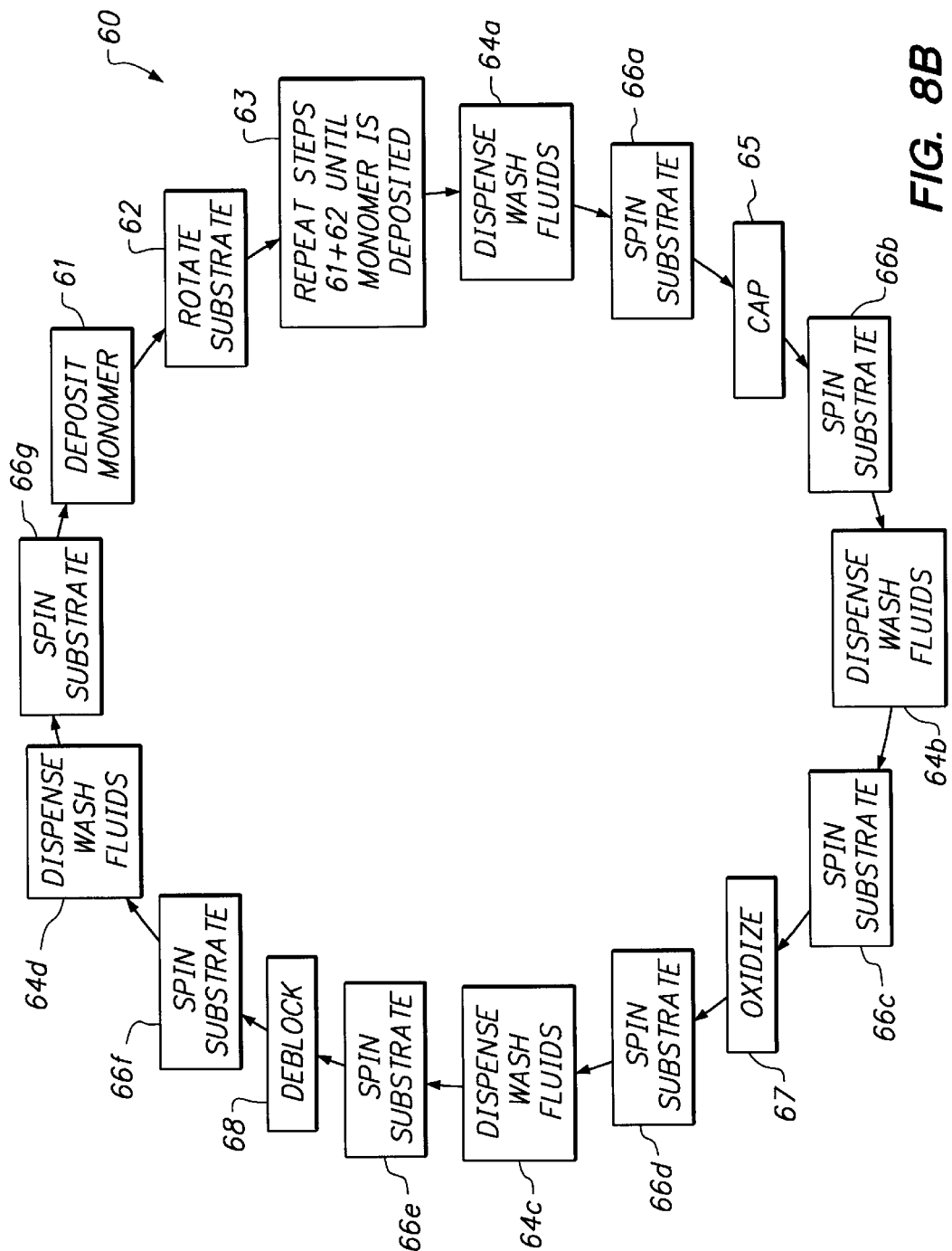

Referring to FIG. 8C, the method 70 of hybridization in accordance with the invention includes introducing the target sample 13b (step 71) into the center 11b of the array substrate surface 12. The array 10 is spun (step 73) by the spinner assembly to move the target sample 13b centrifugically toward the periphery 11a of the substrate 11 where the annular array of probes 13a (15a, 15b, 15c, etc.) is located. In the preferred packaged array 17a embodiment, the target sample 13b is introduced (step 71) into the assay chamber 18b through septum 18c of housing 17, 17b. The sample 13b travels from the chamber 18b directly to the annular cavity region 18a–2 where the probes 13a are located during the spinning step 73.

The amount of target sample 13b available for analysis at any one time is typically very small. Therefore, the target sample 13b should not be wasted during its introduction to the probes 13a for analysis. The present invention advantageously conserves the target sample 13b during the hybridization process. The amount of target sample 13b needed is minimized by the present invention, because the target sample 13b is effectively spread by the centrifugal force of the spinner assembly in a film over the probes 13a in a thickness from approximately 25 to 50 microns. According to the preferred packaged array 17a embodiment, the centrifugal force from spinning (step 73) the packaged array 17a after the target sample 13b is introduced (step 71) into the assay chamber 18b, leaves little or no target sample 13b wasted in the assay chambers 18b, 18a-2 of the housing 17, 17b. Therefore, the use of the valuable target sample 13b, which is typically in very short supply, is optimized in accordance with the present invention.

A conventional hybridization environment is provided (step 75). After the hybridization is completed the hybridized array 10a is spun again (step 77) at a speed high enough so that the excess unhybridized target sample 13b is forced off of the substrate surface 12 by centrifugal force prior to washing the surface. The spin speed used at any one step in the invention is dependent upon the fluids that need to be moved. Basically, the higher the spin speed, the greater the centrifugal force obtained.

In the preferred packaged array 17a embodiment, the unhybridized target sample 13b is moved from the assay chamber 18b to the waste cavity 18a-3 via pathway 18a-4 and first valve chamber 18f-1 by activating the valve assembly 18d therein during the spin step 77. The valve assembly 18d is activated by the centrifugal force of spinning the packaged array 17a at a sufficient speed.

The hybridized array is designated hereinafter as 10a. Ancillary materials, e. g., conventional wash fluids, are then introduced (step 78) to the center of the hybridized array substrate 11 and spun (step 79) across the hybridized array 10a many times until the non-specifically bound (unhybridized) material is removed. The array surface 12 is flooded with wash fluids in a volume of 3 to 10 times the volume of the original target sample 13b introduced. Depending on whether the hybridized array 10a will be optically evaluated in a dry state or wet state, the final wash fluids are either spun out or left in place, respectively.

In the packaged array 17a of the preferred embodiment, the wash fluids are introduced (step 78) into the assay chamber 18b via septum 18c and spun (step 79) at a speed high enough to spread the wash fluids over the hybridized array area 18a-2. The spin step also functions to discharge the wash fluids into at least the first valve chamber 18f-1 via pathway 18a-4. The preferred housing 17b collects and holds the waste of the hybridization procedure in its waste cavity 18a-3. In the preferred packaged array 17a, either the housing 17 or 17b advantageously holds the fluid waste in a controlled fashion. Without the housing 17b in accordance with the preferred embodiment, the fluid waste is collected in the hybridization chamber.

The present invention facilitates automation of the hybridization 71, 75 and washing 78 steps. The transport of ancillary fluid materials is accomplished by centrifugal force inherent in the spinning steps 73, 77, 79. The amount of force applied is controlled by the spinner motor speed. Advantageously, all of the target sample 13b is moved into the probe 13a array area. The target sample 13b is evenly distributed by the spinning motion. No bubbles are formed during the hybridization process, or if they are formed, they are moved to the center of the array 10 during the spinning steps, because they are more buoyant than the fluids. Spreading of reagents, target sample 13b and wash solutions over the surface 12 of the substrate 11 are easily implemented with the spinning steps 73, 77, 79. When the hybridization process is complete, the unhybridized target sample 13b is quickly and cleanly moved out of the probe 13a array area (steps 77–79). The washing steps 77, 78 are completed faster with the invention. The housing 17, 17b of the preferred packaged array 17a embodiment advantageously functions to contain the fluid waste until disposal is appropriate. The valve assemblies 18d in the housing 17, 17b of the preferred packaged array 17a embodiment facilitates the removal of the unhybridized sample and ancillary materials, such as the reagents and washing solutions, and is controlled by centrifugal force.

After the hybridization step of the array 10, the hybridized array 10a is optically interrogated to determine the extent and location of hybridized features 16 among the discrete features 14. In accordance with the invention, the hybridized array 10a is interrogated with an optical scanning system 30 illustrated in FIGS. 4 and 5. The optical scanning system 30 uses either an off-axis method of optical scanning, as described in U.S. Pat. No. 5,585,639, or a confocal method of optical scanning, as described in U.S. Pat. No. 5,760,951 or U.S. Pat. No. 5,763,870 (also describes an autofocus capability), all incorporated herein by reference.

Figure 4:
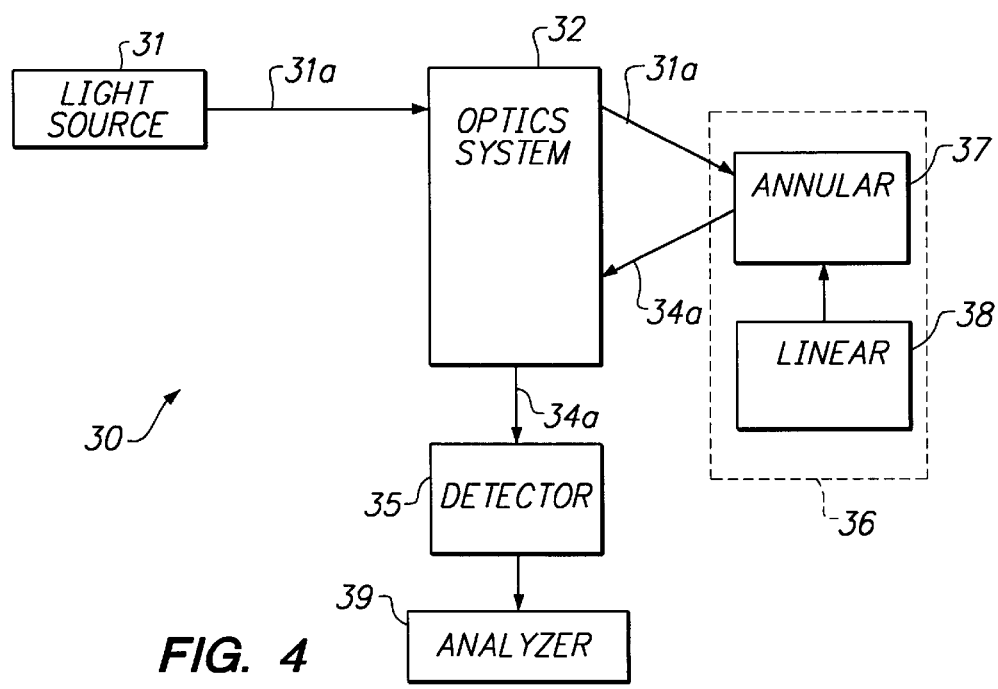
FIG. 4 illustrates a block diagram of the optical scanning system in accordance with the present invention.

Referring to FIG. 4, the optical scanning system 30 of the present invention includes a light source 31, typically a laser, which emits light of a wavelength and with sufficient intensity to cause fluorescence from a fluorophore label. The light beam 31a is focussed and directed by optics subsystem 32 to the hybridized array 10a. A scanning subsystem 36 provides annular movement of the hybridized array 10a in the r, θ format and linear movement to either the array 10a or the optics subsystem 32. A portion of optics subsystem 32 directs a fluorescence signal 34a from the surface of the hybridized array 10a into a detector subsystem 35. The detector subsystem 35 detects the fluorescence signal 34a. The data from the detector subsystem 35 is analyzed by an analysis subsystem 39 and information about the target samples 13b is determined.

The light source 31 may be an Argon ion type laser (off-axis scanner) or an internally doubled Nd-YAG (532 nm) laser and a HeNe (633 nm) laser (confocal scanner). In the preferred embodiment, a confocal scanner with both the internally doubled Nd-YAG (532 nm) and a HeNe (633 nm) laser light source 31 was used.

Figure 5:
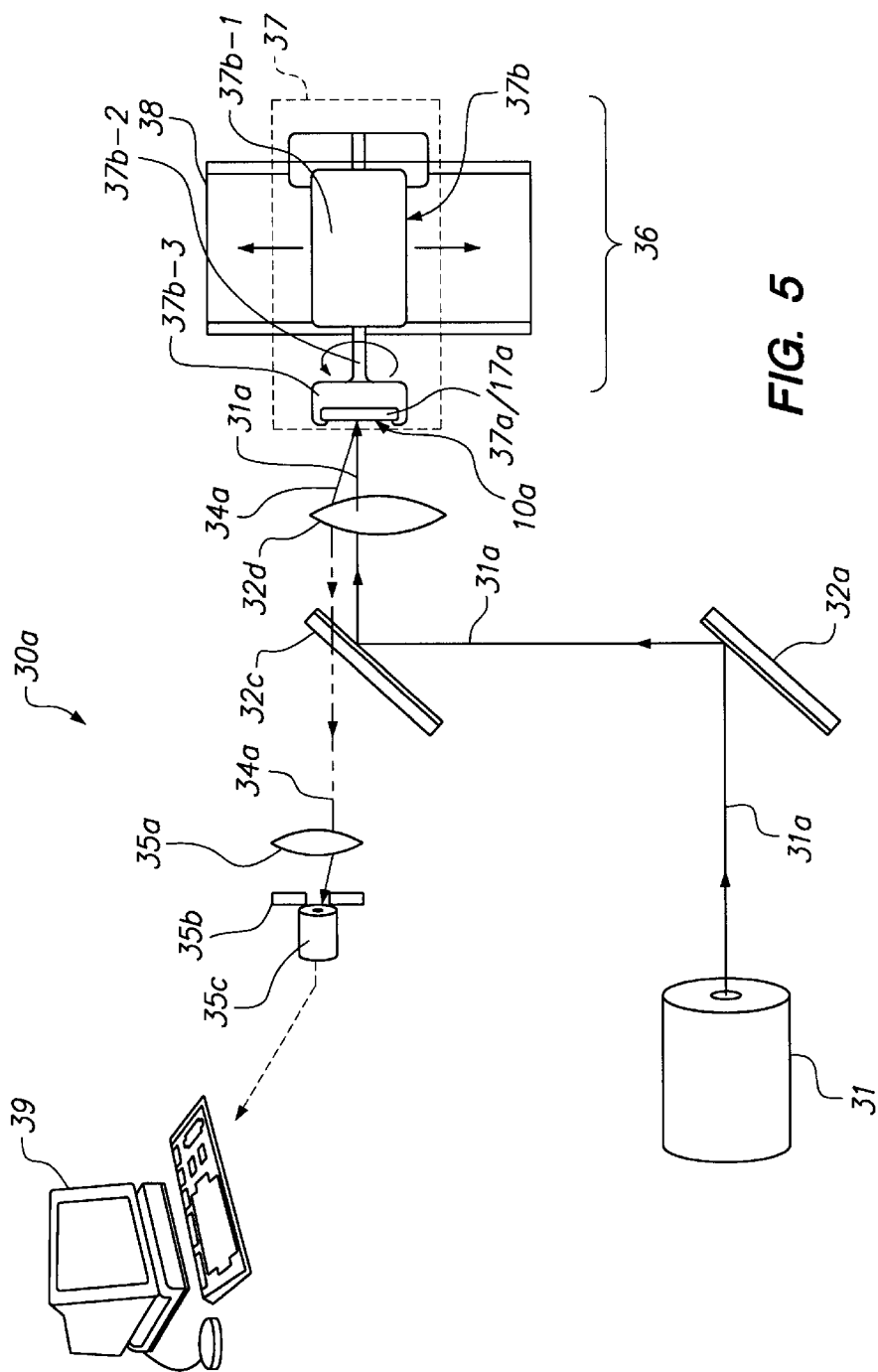
FIG. 5 illustrates a schematic view of the preferred embodiment of the subsystems of FIG. 4 in more detail.
Figure 6:
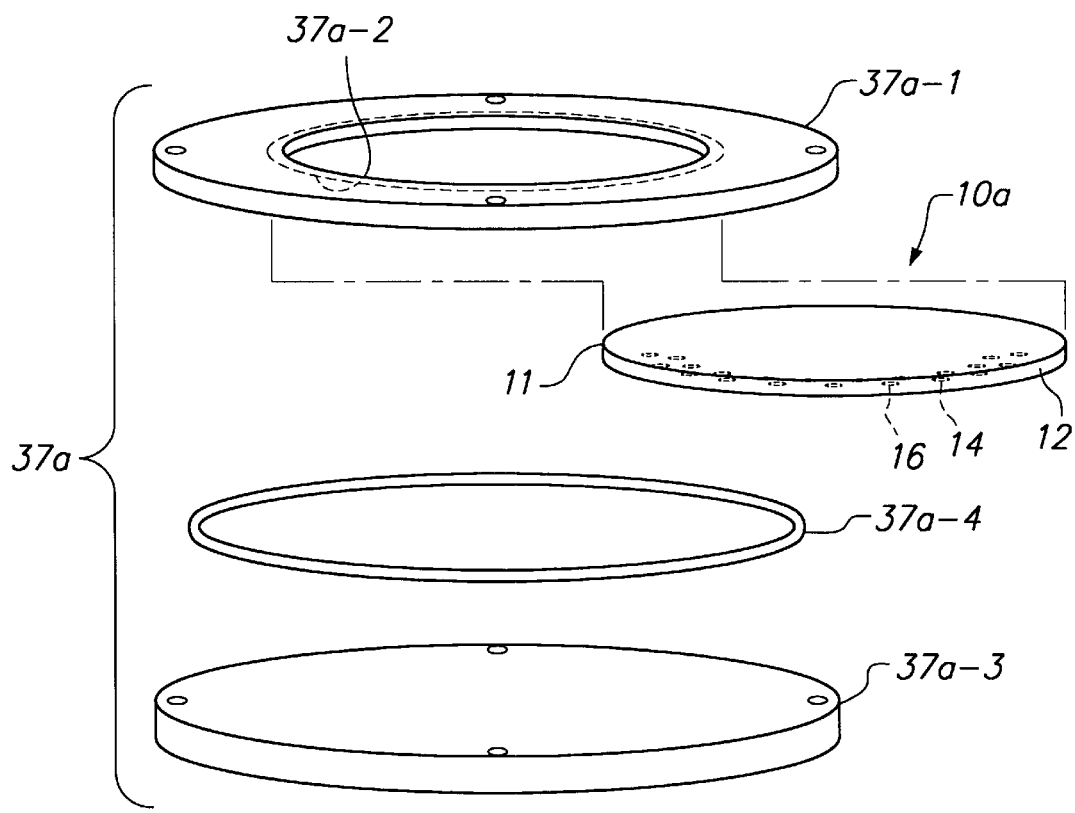
FIG. 6 illustrates an exploded view of the holder that holds the array in accordance to the invention.
Figure 8D:
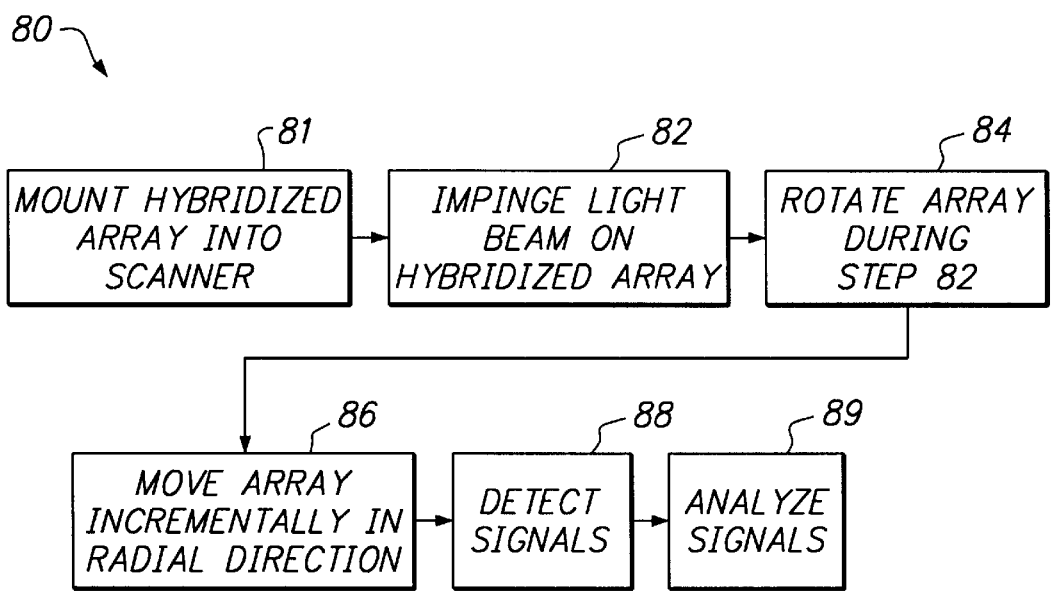

FIG. 5 illustrates a schematic view of the subsystems 32, 35, 36, and 39 of a preferred embodiment of the present scanning system 30. FIG. 8D illustrates the method 80 of optical interrogation in accordance with the invention. The hybridized array 10a is mounted into the scanning subsystem 36 (step 81). The scanning subsystem 36 comprises an annular movement subassembly 37 and a linear movement subassembly 38. The annular movement subassembly 37 comprises a holder 37a for holding the hybridized array 10a in place. An exploded view of the holder 37a is illustrated in FIG. 6. The holder 37a comprises a ring plate 37a-1 having a recess 37a-2 into which the hybridized array 10a is inserted. The holder 37a further comprises a solid plate 37a-3 and an O-ring 37a-4 to seat against the array 10a. The ring plate 37a-1, solid plate 37a-3 and O-ring 37a-4 hold the array 10a flat inside the holder 37a such that the annular array of features 14, 16 are unobstructed and light beam 31a can impinge upon the features 14, 16. The ring plate 37a-1 and solid plate 37a-3 of holder 37a are preferably made of stainless steel and are held together with screws or other appropriate fasteners. In the preferred embodiment, the packaged array 17a is mounted directly into the annular movement subassembly 37 without the need for a holder 37a, as described above.

The annular movement subassembly 37 further comprises a spinner subassembly 37b that provides rotational movement to the holder 37a or the preferred packaged array 17a. The spinner subassembly 37b comprises a spinner motor 37b-1 and a spindle 37b-2, which may be similar to the spinner subassembly 23 in FIG. 2. The spindle 37b-2 has an end 37b-3 for receiving holder 37a or packaged array 17a. The holder 37a or packaged array 17a is removably connected to end 37b-3 of the spindle 37b-2, preferably by way of detents (not shown) so that the holder 37a or the packaged array 17a snaps in and out of the spindle end 37b-3. The spindle 37b-2 is connected for rotational movement at its other end to the spinner motor 37b–1. The spinner subassembly 37b rotates the hybridized array 10a in the holder 37a, or rotates the housing 17, 17b that encloses the array 10a in the preferred packaged array 17a embodiment, while the laser 31, the light source 31a and the optics subsystem 32 remain stationary.

The scanning subsystem 36 further comprises a linear subassembly 38. The linear subassembly 38 comprises a linear actuator (not shown) and a linear stage 38a. The linear subassembly can be used to move the optic subassembly 32 or the annular subassembly 37 in a radial direction. In the preferred embodiment, the spinner subassembly 37b is removably mounted to the linear stage 38a with screws or other appropriate fasteners. The linear subassembly 38 moves the spinner subassembly 37b, along with the hybridized array 10a in holder 37a, or as package array 17a, radially (in FIG. 5, in a direction in or out of the page or along the arrows shown). The movement of the spinner subassembly 37b by the linear subassembly 38 is incremental, in microns, in a radial direction, such that the light beam 31a can scan all of the features 14, 16 in the annular region of the array substrate 11. The linear subassembly 38 does not need to be particularly precise for the present invention, because it provides the radial movement to the spinner subassembly 37b. The linear subassembly 38 can be any commercially available controllable linear system, such as those manufactured by Newport of Irvine, Calif. The present invention was demonstrated with several linear subassemblies from the UTM series of Mid Range Travel Translation Stages.

FIG. 5 further illustrates the light beam 31a from light source 31 entering first optics subsystem 32 where it is reflected by a mirror 32a to a dichroic reflector 32c, where it is directed through an objective lens 32d to impinge (step 82) on the hybridized array 10a. The annular subassembly 37 rotates (step 84) the hybridized array 10a 360 degrees so that the light beam 31a impinges on all of the features 14, 16 in the annular region. The linear subassembly 38 preferably moves the array 10a radially (step 86), so that the light beam 31a impinges on all of the discrete features 14, 16 in the annular region. When the light beam 31a impinges on a fluorophore label on the hybridized features 16, a fluorescence signal 34a is emitted. The fluorescence signal 34a is directed through the objective lens 32d to the dichroic reflector 32c of optics subsystem 32 and the dichroic reflector 32c directs the fluorescence signal 34a into the detector subsystem 35, where the signals 34a are detected (step 88). The detector subsystem 35 comprises a lens 35a, a pinhole or slit 35b to direct the signals 34a into a detector 35c, preferably a photomultiplier tube.

Back reflected light or "signal noise" may also be generated from the surface 12 of the hybridized array 10a substrate 11 in response to the light beam 31a. If generated, the back reflected light also passes through the objective lens 32d, but is filtered out by the dichroic mirror 32c or other filtering means, such as an interference filter, so that the signal noise does not interfere with the detection system 35 and analysis 39.

The detected signals 34a are gathered and analyzed (step 89) by the analysis subsystem 39 comprising a computer. Information about the hybridized targets samples 13b is determined from what is known about the probes 13a at the hybridized locations. Analysis subsystem 39 can use any of the commercially available analysis software programs mentioned previously to analyze the hybridization signals 34a.

In the preferred embodiment, the scanner 30, 30a scans an annulus or ring of about 5 to 10 microns wide then steps over to an adjacent 5 to 10 micron wide annulus to scan until the hybridized array 10a surface 12 is completely scanned in a continuous fashion. Therefore, the scanner 30, 30a scans between discrete features 14, 16, as well as the features 14, 16 themselves. The features 14, 16 are nominally 100 microns in diameter. Therefore, it takes 10–20 scanning rings to scan an annular ring, for example, of features 14, 16. An increased scan speed for rescanning, as described in U.S. Pat. No. 5,837,475, assigned to the assignee of the present invention and incorporated herein by reference, is simply an increase in rotation rate of the spinner subsystem 36 in the preferred embodiment without the acceleration problems of a reciprocating motion scan, as is found in the conventional x, y format scanners described in the U.S. Pat. No. 5,837, 475. In this case, subpixel steps in the radial direction are conceivable. Subpixel scanning is achieved by stepping the scan less than the spot size of the light beam 31a.

The optical scanning system 30 of the present invention provides for faster scan processing. There is a 100 percent duty cycle during the scan because overscanning is limited to compensating for run-out, which may occur during the manufacturing process. Run out is a term that defines possible alignment errors during manufacturing of the array 10 rendering the array pattern slightly off center. The present invention looks at the entire range of possible manufacturing errors to be sure that the actual array of features 14, 16 is scanned completely.

The present optical scanning system 30 and method 80 have no direction changes between scan lines, as found in the conventional x, y format scanners mentioned above. There is no risk of the laser beam 31a impinging on adhesive glue lines, since the scan is circular. The instrumentation for the optical scanning system 30 is less expensive than the conventional systems for comparable performance, because neither an x, y stage nor a galvanometer is required. Moreover, since the centrifugal force from spinning during the hybridization method 70 eliminates bubbles or spins the bubbles out of the scanned region, the present invention interrogation system 30 and method 80 provide more reliable results. The movement of the hybridized array 10a rather than the optics 32 or the laser assembly 31 allows for a very small, high depth discrimination lens 32d at a reasonable cost. In addition, the present optical scanning system 30 and method 80 facilitate dynamic autofocussing, as described in U.S. Pat. No. 5,763,870.

Figure 7:
FIG. 7 illustrates an output from the optical scanner of a hybridized annular array in accordance with the invention.

FIG. 7 illustrates an example of the analysis obtained from analysis subsystem 39 of a hybridized array 10a. The hybridization results in FIG. 7 are merely illustrative of the many hybridization scenarios possible in a biological assay. The results illustrated in FIG. 7 are not intended to limit the scope of the invention or to represent a preferred embodiment of the invention. It should be understood by those skilled in the art that the hybridization efficiency between the probes 13a and the target nucleotide sequences 13b is dependent upon their complementarity and the hybridization processes used, among other things.

Moreover, the hybridization results in FIG. 7 are presented in a linear mode. Each circular sweep made by the substrate 11 while the light beam is impinging on the surface is translated to a straight line at the output of the analysis subsystem 39. It is not the intent of the inventors to be limited to a linear representation of the hybridization results and the results can be presented in any format and still be within the scope of the invention.

FIGS. 8A illustrates the method 50 of assaying biological materials in accordance with the present invention. Referring to FIG. 8A, a first biological material, such as the oligonucleotide probes 13a, are provided (step 51) on the substrate 11 in an annular array pattern of discrete features 14 with the synthesis system 20 and synthesis method 60 of the present invention. A second biological material, such as the target nucleotide sequences or sample 13b, is hybridized (step 53) with the probes 13a with the hybridization system and method 70 of the present invention. The hybridized discrete features 16 have a signal producing system for producing a signal 34a when illuminated with a light beam 31a. As mentioned above, the signal producing system can be a conventional label, and preferably a fluorophore label.

The hybridized array 10a is optically interrogated (step 55) with the optical interrogation system 30 and method 80 of the present invention. The information obtained from the fluorescence signals 34a is used to determine (step 57) the characteristics about the first biological material 13a and the second biological material 13b.

The method 50 of assaying biological materials 13 is particularly conducive to automation and therefore, has inherent advantages. Each step 51–57 of the assay process mentioned above can be automated to provide flexibility and accuracy to the assaying process 50.

Thus there has been described a new apparatus, systems and methods for assaying biological materials that uses an r, θ format. The biological array apparatus is manufactured on a substrate and the annular array pattern is interrogated optically in the r, θ format using an optical scanning system that rotates or spins the array 360 degrees and moves the array or the optics in a radially fashion. It should be understood that the above-described embodiments are merely illustrative of the some of the many specific embodiments that represent the principles of the present invention. Clearly, numerous other arrangements can be readily devised by those skilled in the art without departing from the scope of the present invention.

For example, the array 10 of the invention is not limited to a particular size or array substrate thickness. The array substrate 10 need not be circular, as long as the array pattern of surface bound features is within an annular region of the substrate and the synthesis, hybridization or optical interrogation of the array can take advantage of the rotational motion in the r, θ format, It is within the scope of the present invention to use a variety of substrate shapes, diameters and thicknesses. Moreover, the array substrate does not have to be clear. Substrates that are opaque are within the scope of the invention. Opaque substrates can be scanned from the array side as opposed to scanning through the clear substrate material to the array. As mentioned above, packaging the array is a preferred embodiment and the array does not have to be packaged in accordance with the invention. Moreover, the array pattern can be arranged in any annular pattern, including but not limited to a spiral or concentric and/or segmented annular rings and still be within the scope of the invention. It is also within the scope of the invention to manufacture the array by printing the monomers with an x, y format system during in situ synthesis, but optically scan the array in an annular fashion. Moreover, the features could be printed in the x, y format in a closely packed pattern that approximates a circle, where the center of the pattern is missing. This pattern would allow for x, y deposition of pre-synthesized DNA and annular scanning using the present invention.

What is claimed is:

1. An apparatus for assaying biological materials comprising:
    a substrate having a surface, an outer edge and a center; and
    a plurality of discrete features bound to the surface of the substrate in an annular pattern, the plurality of discrete features comprising a first biological material, wherein the annular pattern is a spiral pattern having one end adjacent to the outer edge of the substrate and an opposite end adjacent to the center of the substrate.

2. The apparatus of claim 1, wherein the substrate has a circular shape.

3. An apparatus for assaying biological materials comprising:
    a substrate having a surface;
    a plurality of discrete features bound to the surface of the substrate in an annular pattern, the plurality of discrete features comprising a first biological material; and
    a housing for holding the substrate and the plurality of discrete features bound to the substrate surface, the housing comprising a valve assembly and a plate, the plate having an outer edge, a first side and a second side opposite to the first side, wherein the plate comprises:
        a port extending from the first side to the second side of the plate,
        a first recess in the first side coaxial with the port,
        a second recess in the first side having an annular shape and being coaxial with the first recess,
        a third recess in the first side having an annular shape and being coaxial with the second recess, the third recess for receiving the substrate, wherein the first recess and the second recess in the plate and the substrate define a chamber in the housing for receiving the second biological material and ancillary materials through the port, the plurality of discrete features being adjacent to a region in the chamber corresponding to the second recess and being visible from the first side of the plate; and
        a recess extending radially from the outer edge of the plate inward being in communication with the second recess; and
    wherein the valve assembly is located in the radially extending recess, the valve assembly comprising an actuator, a biasing means, and a cap, the cap being attached to the outer edge of the plate such that the radially extending recess forms a valve chamber inside the plate.

4. The apparatus of claim 1, wherein the plurality of discrete features further comprises:
    a second biological material chemically associated with the first biological material; and
    a signal producing system chemically associated with the plurality of discrete features.

5. The apparatus of claim 4, wherein the second biological material is complementary to the first biological material.

6. The apparatus of claim 5, wherein the first biological material is an oligonucleotide probe and the second biological material is a target nucleotide sequence.

7. The apparatus of claim 3, wherein the annular pattern is a plurality of annular rings.

8. The apparatus of claim 7, wherein the plurality of annular rings are concentric annular rings of decreasing diameter from the outer edge of the substrate to the center.

9. The apparatus of claim 8, wherein the plurality of annular rings are segmented.

10. The apparatus of claim 3, wherein the annular pattern is a spiral pattern having one end adjacent to the outer edge of the substrate and an opposite end adjacent to the center of the substrate.

11. The apparatus of claim 1, further comprising a housing for holding the substrate and the plurality of discrete features bound to the substrate surface.

12. The apparatus of claim 11, wherein the housing comprises:
    a plate having an outer edge, a first side and a second side opposite to the first side, the plate comprising:
        a port extending from the first side to the second side of the plate, a first recess in the first side coaxial with the port, a second recess in the first side having an annular shape and being coaxial with the first recess, a third recess in the first side having an annular shape and being coaxial with the second recess, the third recess for receiving the substrate, wherein the first recess and the second recess in the plate and the substrate define a chamber in the housing for receiving the second biological material and ancillary materials through the port, the plurality of discrete features being adjacent to a region in the chamber corresponding to the second recess and being visible from the first side of the plate; and a recess extending radially from the outer edge of the plate inward being in communication with the second recess; and a valve assembly in the radially extending recess, the valve assembly comprising an actuator, a biasing means and a cap, the cap being attached to the outer edge of the plate such that the radially extending recess forms a valve chamber inside the plate.

13. The apparatus of claim 12, wherein the port comprises a septum for allowing the second biological material and ancillary materials to pass into the chamber, the septum preventing the materials from exiting the chamber through the port.

14. The apparatus of claim 12, wherein the housing further comprises:

a second radially extending recess located diametrically opposite to said radially extending recess;

a second valve assembly similar to said valve assembly enclosed in the second radially extending recess;

a fourth recess in the second side of the plate having an annular shape; and a ring frame attached to the second side of the plate, the ring frame enclosing the fourth recess, the fourth recess and the ring frame forming an annular cavity within the housing, wherein said radially extending recess and the second radially extending recess intersect with the fourth recess and are in communication with the annular cavity, and wherein at least one of said radially extending recess and the second radially extending recess is in communication with the exterior of the plate adjacent to the second side.

15. The apparatus of claim 3, wherein the port comprises a septum for allowing the second biological material and ancillary materials to pass into the chamber, the septum preventing the materials from exiting the chamber through the port.

16. The apparatus of claim 3, wherein the housing further comprises:

a second radially extending recess located diametrically opposite to said radially extending recess;

a second valve assembly similar to said valve assembly enclosed in the second radially extending recess;

a fourth recess in the second side of the plate having an annular shape; and a ring frame attached to the second side of the plate, the ring frame enclosing the fourth recess, the fourth recess and the ring frame forming an annular cavity within the housing, wherein said radially extending recess and the second radially extending recess intersect with the fourth recess and are in communication with the annular cavity, and wherein at least one of said radially extending recess and the second radially extending recess is in communication with the exterior of the plate adjacent to the second side.

17. The apparatus of claim 3, wherein the substrate has a circular shape.

18. The apparatus of claim 11 wherein he substrate has a circular shape.

19. The apparatus of claim 3, wherein the plurality of discrete features further comprises:

a second biological material chemically associated with the first biological material; and a signal producing system chemically associated with the plurality of discrete features.

20. The apparatus of claim 19, wherein the second biological material is complementary to the first biological material.

21. The apparatus of claim 20, wherein the first biological material is an oligonucleotide probe and the second biological material is a target nucleotide sequence.

* * * * *